(12) United States Patent
Jensen et al.

(10) Patent No.: US 12,427,150 B2
(45) Date of Patent: Sep. 30, 2025

(54) PHOSPHOLIPID FORMULATIONS OF 1'-CYANO SUBSTITUTED CARBA-NUCLEOSIDE ANALOGS

(71) Applicant: Gilead Sciences, Inc., Foster City, CA (US)

(72) Inventors: Gerard Jensen, Brea, CA (US); Youngri Kim, Anaheim, CA (US); Kian Yong Lee, Diamond Bar, CA (US); Huy Pham, Orange, CA (US); Thomas Upton, Huntington Beach, CA (US); Stephanie Yang, Arcadia, CA (US)

(73) Assignee: Gilead Sciences, Inc., Foster City, CA (US)

( * ) Notice: Subject to any disclaimer, the term of this patent is extended or adjusted under 35 U.S.C. 154(b) by 408 days.

(21) Appl. No.: 17/824,288

(22) Filed: May 25, 2022

(65) Prior Publication Data

US 2023/0000873 A1    Jan. 5, 2023

Related U.S. Application Data

(60) Provisional application No. 63/193,510, filed on May 26, 2021.

(51) Int. Cl.
*A61K 31/519* (2006.01)
*A61K 9/00* (2006.01)
(Continued)

(52) U.S. Cl.
CPC .......... *A61K 31/519* (2013.01); *A61K 9/0019* (2013.01); *A61K 9/1682* (2013.01);
(Continued)

(58) Field of Classification Search
CPC ... A61K 31/519; A61K 31/685; A61K 47/544
See application file for complete search history.

(56) References Cited

FOREIGN PATENT DOCUMENTS

| CN | 111991375 A | 11/2020 |
|---|---|---|
| WO | WO-2005070465 A2 | 8/2005 |
| WO | WO-2017184668 A1 | 10/2017 |

OTHER PUBLICATIONS

Google English translation of CN111991375 (Year: 2020).*
(Continued)

*Primary Examiner* — San Ming R Hui

(57) ABSTRACT

The disclosure provides pharmaceutical formulations of the compound of Formula I:

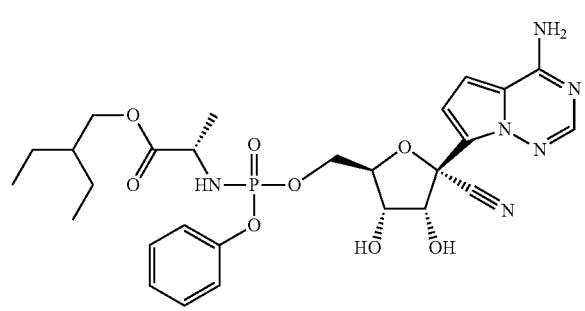

Formula I or a pharmaceutically acceptable salt thereof.

33 Claims, 6 Drawing Sheets

(51) Int. Cl.
*A61K 9/16* (2006.01)
*A61K 31/685* (2006.01)
*A61K 47/26* (2006.01)
*A61K 47/54* (2017.01)

(52) U.S. Cl.
CPC ............ *A61K 31/685* (2013.01); *A61K 47/26* (2013.01); *A61K 47/542* (2017.08); *A61K 47/544* (2017.08)

(56) References Cited

OTHER PUBLICATIONS

International Preliminary Report on Patentability dated Nov. 21, 2023 for Int'l Application No. PCT/US2022/030866.
International Search Report & Written Opinion dated Sep. 26, 2022 for Int'l Application No. PCT/US2022/030866.
Li, J. et al. (2015) "A review on phospholipids and their main applications in drug delivery systems" Asian Journal of Pharmaceutical Sciences, 10:81-98.
Agostini, M. et al. (2018) "Coronavirus Susceptibility to the Antiviral Remdesivir (GS5734) Is Mediated by the Viral Polymerase and the Proofreading Exoribonuclease" American Society for Microbiology, 9:2, 15 pages.
Jensen, G. et al. (2008) "A liposomal dispersion formulation of propofol: formulation, pharmacokinetics, stability, and identification of an oxidative degradant" Theor Chem Account, 119: 291-296.
Lo, M. et al. (2017) "GS-5734 and its parent nucleoside analog inhibit Filo-, Pneumo-, and Paramyxoviruses" Nature, Scientific Reports, 7 pages.
Sheahan, T. et al. (2017) "Broad-spectrum antiviral GS-5734 inhibits both epidemic and zoonotic coronaviruses" Science Translation Medicine, 9: 1-10.
Wang, M. et al. (2020) "Remdesivir and chloroquine effectively inhibit the recently emerged novel coronavirus (2019-nCoV) in vitro" Cell Research, 30:269-271.
Warren, T. et al. (2016) "Therapeutic efficacy of the small molecule GS-5734 against Ebola virus in rhesus monkeys" Nature, 531: 19 pages.

* cited by examiner

PHOSPHOLIPID FORMULATIONS OF 1'-CYANO SUBSTITUTED CARBA-NUCLEOSIDE ANALOGS

CROSS REFERENCE TO RELATED APPLICATIONS

This application claims priority to the U.S. Provisional Application No. 63/193,510 filed May 26, 2021, which application is incorporated herein by reference in its entirety for all purposes.

FIELD

Provided are pharmaceutical formulations suitable for treating viral infections such as Arenaviridae, Coronaviridae, Filoviridae, Flaviviridae, Orthomyxoviridae, Pneumoviridae, or Paramyxoviridae viral infections. In particular, provided herein are phospholipid formulations comprising the compound of Formula I, Formula Ia, or Formula Ib as described herein, or a pharmaceutically acceptable salt thereof.

BACKGROUND

Preventing or treating some Arenaviridae, Coronaviridae, Filoviridae, Flaviviridae, Orthomyxovirus, Pneumoviridae, and Paramyxoviridae viral infections present challenges due to a lack of vaccine or post-exposure treatment modality for preventing or managing infections caused by viruses from these families. In some cases, patients only receive supportive therapy such as electrolyte and fluid balancing, oxygen, blood pressure maintenance, or treatment for secondary infections.

The compound (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate, referred to herein as the compound of Formula Ia, is known to exhibit antiviral properties against several viral families, including Arenaviridae, Coronaviridae, Filoviridae, Paramyxoviridae, and Flaviviridae viruses (see e.g., Warren, T. et al., Nature (2016) 531:381-385; Lo M K, et al. Sci. Reports 2017; 7:43395; Sheahan T P, et al. Sci. Transl. Med. 2017; 9:eaal3653; Agostini M L, et al. MBio 2018; 9(2):e00221-18; Cell Research (2020) 30:269-271, and WO 2017/184668). There is a need to develop pharmaceutical formulations comprising the compound of Formula Ia, or a pharmaceutically acceptable salt thereof. Such pharmaceutical formulations can be useful, especially in treatment of viral infections, for e.g., respiratory infection.

SUMMARY OF THE INVENTION

In some embodiments, the disclosure provides a pharmaceutical formulation comprising:
a. phospholipids; and
b. a compound of Formula I:

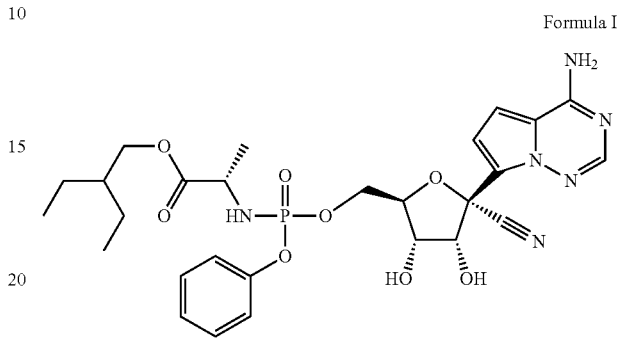

Formula I or a pharmaceutically acceptable salt thereof;
wherein the phospholipids comprise a phosphatidyl choline and an anionic phospholipid.

In some embodiments, the disclosure provides a method of treating or preventing a viral infection in a human in need thereof, wherein the method comprises administering to the human the pharmaceutical formulation of the disclosure.

In some embodiments, the disclosure provides use of a pharmaceutical formulation disclosed herein, for the manufacture of a medicament for the treatment or prevention of a viral infection in a human in need thereof.

DETAILED DESCRIPTION

I. General

Figure 1:
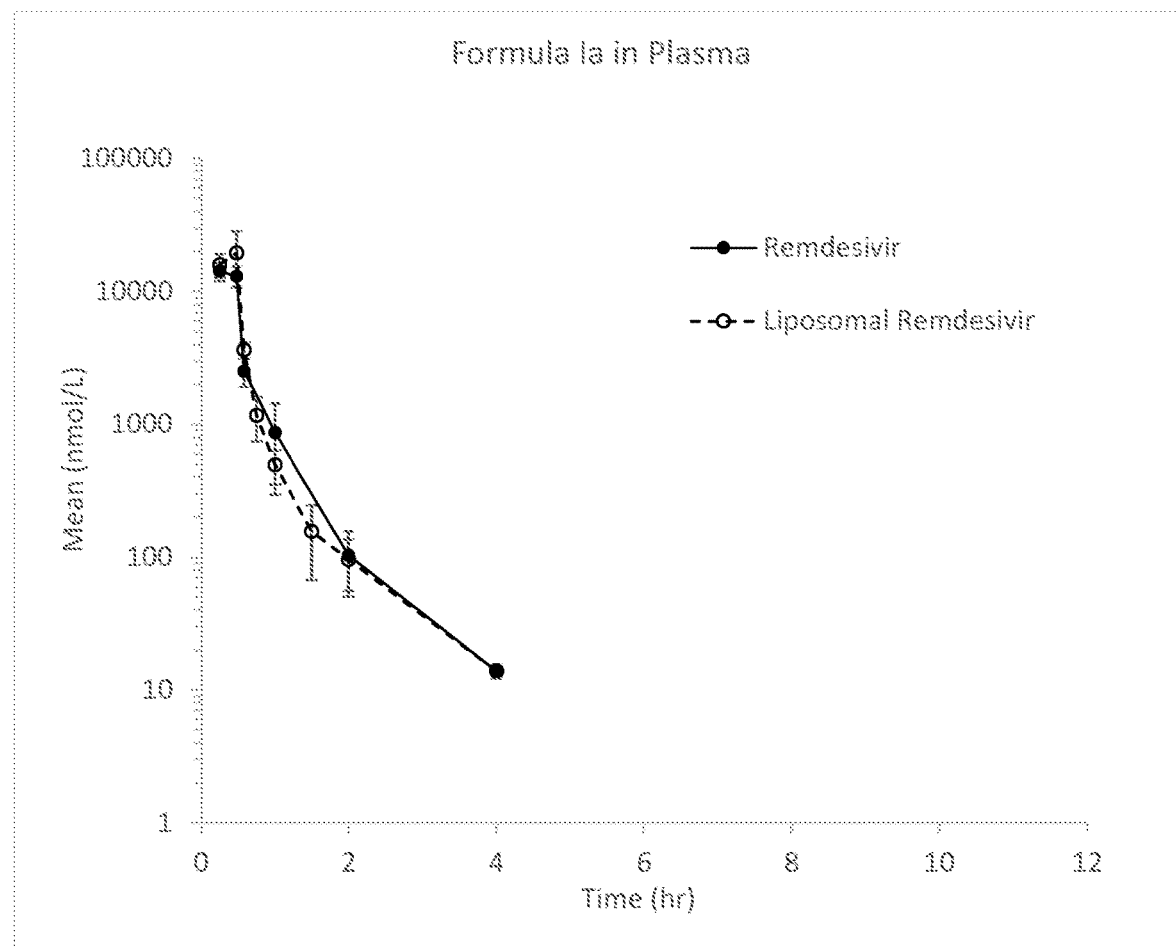
FIG. 1. Shows concentration-time profiles of the compound of Formula Ia in plasma following administration of an exemplary pharmaceutical formulation (10 mg/kg dosing of the compound of Formula Ia) to Cynomolgus monkeys.

Provided are pharmaceutical formulations suitable for treating viral infections such as Arenaviridae, Coronaviridae, Filoviridae, Flaviviridae, Orthomyxoviridae, Pneumoviridae, or Paramyxoviridae viral infections. In particular, provided herein are phospholipid formulations comprising the compound of Formula I, Formula Ia, or Formula Ib as described herein, or a pharmaceutically acceptable salt thereof.

II. Definitions

"The compound of Formula I" refers to the following compound:

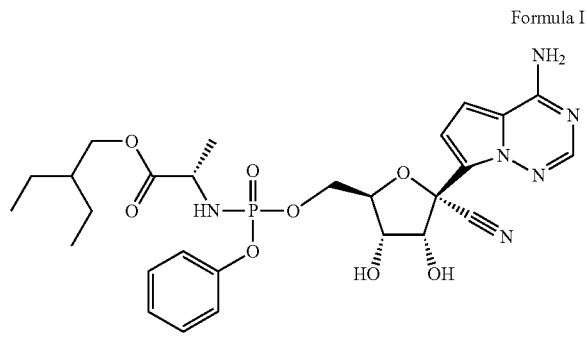 [SMILES: CCC(CC)COC(=O)[C@H](C)NP(=O)(OC[C@H]1O[C@@](C#N)(c2ccc3c(N)ncnn23)[C@H](O)[C@@H]1O)Oc1ccccc1]

Formula I

The compound of Formula I was disclosed in WO2012/012776. The IUPAC name for the compound of Formula I is 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate.

"The compound of Formula Ia" refers to the following compound:

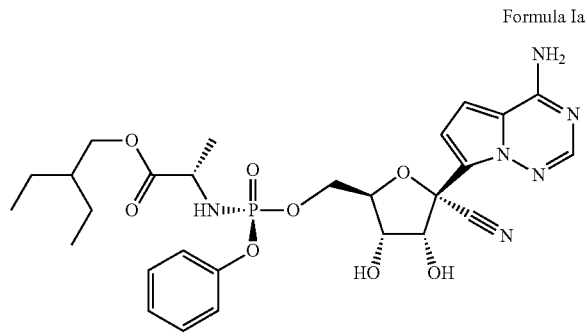 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Formula Ia

The compound of Formula Ia is disclosed in WO2016/069826. The IUPAC name for the compound of Formula Ia is (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino) propanoate, and the CAS Registry Number is 1809249-37-3. The compound of Formula Ia is also referred to as remdesivir and GS-5734.

"The compound of Formula Ib" refers to the following compound:

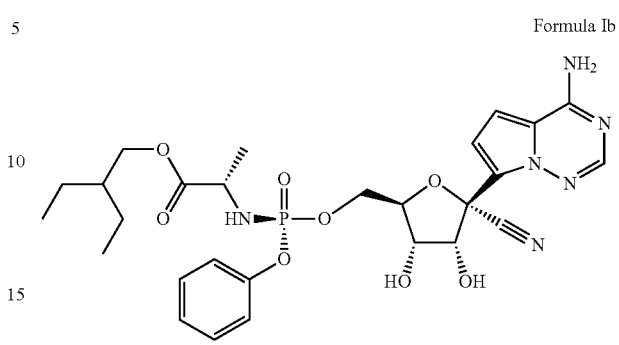

Formula Ib

The compound of Formula Ib is disclosed in WO2016/069826. The IUPAC name for the compound of Formula Ib is (S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino) propanoate.

The compounds of the disclosure, exemplified by Formula I, Formula Ia and Formula Ib have chiral centers, e.g., chiral carbon or phosphorus atoms. The compounds of the disclosure thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including compounds of Formula I, Formula Ia, or Formula Ib, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to 2H (deuterium, D), 3H (tritium), 11C, 13C, 14C, 15N, 18F, 31P, 32P, 35S, 36Cl and 125I. Various isotopically labeled compounds of the present disclosure, for example those into which radioactive isotopes such as 3H, 13C and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, Formula Ia, and Formula Ib in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I, Formula Ia, and Formula Ib when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An 18F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, Formula Ia, and Formula Ib.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compositions may, in some embodiments, be administered to a subject (including a human) who is at risk or has a family history of the disease or condition.

III. Pharmaceutical Formulations

All formulations described herein comprise a compound of Formula I, or a pharmaceutically acceptable salt thereof, and phospholipids, wherein the phospholipids comprise a phosphatidyl choline and an anionic phospholipid. In some embodiments, the pharmaceutical formulations provided herein comprise the compound of Formula Ia, or a pharmaceutically acceptable salt thereof and phospholipids, wherein the phospholipids comprise a phosphatidyl choline and an anionic phospholipid. In some embodiments, the pharmaceutical formulations provided herein comprise the compound of Formula Ib, or a pharmaceutically acceptable salt thereof and phospholipids, wherein the phospholipids comprise a phosphatidyl choline and an anionic phospholipid.

1. The Compound of Formula I, Formula Ia, and Formula Ib

The compound of Formula I, Formula Ta, or Formula Ib can be used in any suitable form. For example, the compound of Formula I, Formula Ta, or Formula Ib can be amorphous or crystalline. In some embodiments, the compound of Formula I, Formula Ta, or Formula Ib is amorphous. In some embodiments, the compound of Formula I, Formula Ta, or Formula Ib is crystalline.

Crystalline forms of the compound of Formula Ta useful in the methods and compositions of the present invention are described in U.S. Patent Application Publication No. 20180346504. For example, the compound of Formula Ta can be crystalline Form I, Form II, Form III, Form IV as described in U.S. Patent Application Publication No. 20180346504, or a combination thereof. In some embodiments, the compound of Formula Ta is crystalline.

In some embodiments, the compound of Formula Ia is crystalline Form II. In some embodiments, crystalline compound of Formula Ia is characterized by an X-ray powder diffraction (XRPD) pattern having at least three peaks selected from the group consisting of 22.3°, 16.2°, 22.5°, 13.8°, 12.7°, 16.9°, 10.6°, 14.5°, 24.3, 24.0°, 17.6°, 23.4°, 8.1°, 11.0°, 26.8°, 28.9°, 19.6°, 27.8°, 26.4°, 28.7°, 29.8°, 33.0°, 18.8°, 18.3°, 32.1°, 25.3°, 32.6°, 8.6°, 34.2°, 35.9°, 27.2°, 28.1°, 38.9°, 34.6°, 17.1°, 35.2°, 21.4°, 30.6°, 25.6°, 18.5°, 31.7°, 36.5°, and 37.1°±0.2° 2-θ.

In some embodiments, crystalline Form II of the compound of Formula Ia has an XRPD pattern comprising degree 2θ-reflections (+/−0.2 degrees 2θ) at 22.3°, 16.9°, and 16.2°. In some embodiments, crystalline Form II of the compound of Formula Ia has an XRPD pattern comprising degree 2θ-reflections (+/−0.2 degrees 2θ) at 22.3°, 16.9°, and 16.2° and one or more of the degree 2θ-reflections (+/−0.2 degrees 2θ) at 13.8° and 12.7°. In some embodiments, crystalline Form II of the compound of Formula Ia has an XRPD pattern comprising degree 2θ-reflections (+/−0.2 degrees 2θ) at 22.3°, 16.9°, and 16.2° and one of the degree 2θ-reflections (+/−0.2 degrees 2θ) at 13.8° and 12.7°. In some embodiments, crystalline Form II of the compound of Formula Ia has an XRPD pattern comprising degree 2θ-reflections (+/−0.2 degrees 2θ) at 22.3°, 16.9°, and 16.2° and two of the degree 2θ-reflections (+/−0.2 degrees 2θ) at 13.8° and 12.7°. In some embodiments, crystalline Form II the compound of Formula Ia has an XRPD pattern comprising degree 2θ-reflections (+/−0.2 degrees 2θ) at 22.3°, 16.9°, 16.2°, 13.8° and 12.7°. In some embodiments, crystalline Form II the compound of Formula Ia has an XRPD pattern comprising any three degree 2θ-reflections (+/−0.2 degrees 2θ) selected from the group consisting of 22.3°, 16.9°, 16.2°, 13.8°, and 12.7°.

In some embodiments, crystalline Form II of the compound of Formula Ia has an XRPD pattern further comprising degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8° and 12.7° and one or more of the degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8° and 12.7° and one of the degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8° and 12.7° and two of the degree 2θ-reflections (+/−0.2 degrees 2θ) at 22.5°, 10.6° and 14.5°. In some embodiments, crystalline Form II of the compound of Formula Ia has an XRPD pattern comprising degree 2θ-reflections (+/−0.2 degrees 2θ) at 22.3°, 16.9°, 16.2°, 13.8°, 12.7°, 22.5°, 10.6° and 14.5°. In some embodiments, crystalline Form II of the compound of Formula Ia has an XRPD pattern comprising any three degree 2θ-reflections (+/−0.2 degrees 2θ) selected from the group consisting of 22.3°, 16.9°, 16.2°, 13.8°, 12.7°, 22.5°, 10.6° and 14.5°.

In some embodiments, the compound of Formula Ia is a mixture of crystalline Form II and crystalline Form IV. In some embodiments, the compound of Formula Ia is Mixture I, Mixture II, or Mixture III as described in in U.S. Patent Application Publication No. 20180346504.

In some embodiments, the compound of Formula Ia is Mixture I having an XRPD pattern comprising degree 2θ-reflections (+/−0.2 degrees 2θ) at 15.9°, 22.6°, and 14.1°. In some embodiments, Mixture I has an XRPD pattern comprising degree 2θ-reflections (+/−0.2 degrees 2θ) at 15.9°, 22.6°, and 14.10 and the degree 2θ-reflection (+/−0.2 degrees 2θ) at 12.5°. In some embodiments, Mixture I has an XRPD pattern comprising degree 2θ-reflections (+/−0.2 degrees 2θ) at 15.9°, 22.6°, 14.1°, and 12.5°. In some embodiments, Mixture I has an XRPD pattern comprising any three degree 2θ-reflections (+/−0.2 degrees 2θ) selected from the group consisting of 15.9°, 22.6°, 14.1°, and 12.5°.

In some embodiments, the compound of Formula Ia is Mixture II having an XRPD pattern comprising degree 2θ-reflections (+/−0.2 degrees 2θ) at 16.1°, 22.4°, and 12.7°. In some embodiments, Mixture II has an XRPD pattern comprising degree 2θ-reflections (+/−0.2 degrees 2θ) at 16.1°, 22.4°, and 12.7° and one or more of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and one of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and two of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, and 12.7° and three of the degree 2θ-reflections (+/−0.2 degrees 2θ) at 24.2°, 16.8°, and 8.1°. In some embodiments, Mixture II has an XRPD pattern comprising degree 2θ-reflections (+/−0.2 degrees 2θ) at 16.1°, 22.4°, 12.7°, 24.2°, 16.8°, and 8.1°. In some embodiments, Mixture II has an XRPD pattern comprising any three degree 2θ-reflections (+/−0.2 degrees 2θ) selected from the group consisting of 16.1°, 22.4°, 12.7°, 24.2°, 16.8°, 8.1°, 13.9°, 17.5°, 11.1°, 10.7°, 14.7°, and 19.8°.

In some embodiments, the compound of Formula Ia is Mixture III having an XRPD pattern comprising degree 2θ-reflections (+/−0.2 degrees 2θ) at 16.7°, 12.6°, and 17.2°. In some embodiments, Mixture III has an XRPD pattern comprising degree 2θ-reflections (+/−0.2 degrees 2θ) at 16.7°, 12.6°, and 17.2° and one or more of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, and 17.2° and one of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, and 17.2° and two of the degree 2θ-reflections (+/−0.2 degrees 2θ) at 19.6° and 14.1°. In some embodiments, Mixture III has an XRPD pattern comprising degree 2θ-reflections (+/−0.2 degrees 2θ) at 16.7°, 12.6°, 17.2°, 19.6° and 14.1°. In some embodiments, Mixture III has an XRPD pattern comprising any three degree 2θ-reflections (+/−0.2 degrees 2θ) selected from the group consisting of 16.7°, 12.6°, 17.2°, 19.6° and 14.1°.

The compound of Formula I, Formula Ia, or Formula Ib can have any suitable purity. For example, the compound of Formula I, Formula Ia, or Formula Ib can have a purity of at least about 90%, or at least about 91%, about 92%, about 93%, about 94%, about 95%, about 96%, about 97%, about 98%, about 99%, or at least about 99.1%, about 99.2%, about 99.3%, about 99.4%, about 99.5%, about 99.6%, about 99.7%, about 99.8% or at least about 99.9%. In some embodiments, the compound of Formula I, Formula Ia, or Formula Ib has a purity of at least about 99.1%. In some embodiments, the compound of Formula I, Formula Ia, or Formula Ib has a purity of at least about 99.3%. In some embodiments, the compound of Formula I, Formula Ia, or Formula Ib has a purity of at least about 99.5%. In some embodiments, the compound of Formula I, Formula Ia, or Formula Ib has a purity of at least about 99.7%.

The impurities present in the compound of Formula I, Formula Ia, or Formula Ib can include unreacted starting material, undesirable side-products, and other materials. Representative impurities include Impurity A (also referred as Compound A):

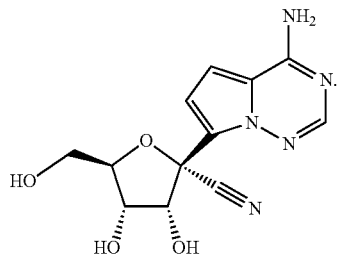 [SMILES: N#C[C@@]1(c2ccc3c(N)ncnn23)O[C@H](CO)[C@@H](O)[C@H]1O]

Impurity A can be present in an amount less than about 0.5%, or less than about 0.45%, about 0.40%, about 0.35%, about 0.30%, about 0.25%, about 0.20%, about 0.15%, about 0.10%, about 0.09%, about 0.08%, about 0.07%, about 0.06%, about 0.05%, about 0.04%, about 0.03%, about 0.02%, or less than about 0.01%. The amount of Impurity A can be measured in % AN (% area normalization) as measured by HPLC, or can be based on weight (w/w). In some embodiments, the compound of Formula I, Formula Ia, or Formula Ib includes less than about 0.10% Impurity A. In some embodiments, the compound of Formula I, Formula Ia, or Formula Ib includes less than about 0.05% Impurity A.

In some embodiments, the compound of Formula I, Formula Ia, or Formula Ib can have a purity of at least about 99.1%, and include less than about 0.10% Impurity A. In some embodiments, the compound of Formula I, Formula Ia, or Formula Ib can have a purity of at least about 99.1%, and include less than about 0.05% Impurity A. In some embodiments, the compound of Formula I, Formula Ia, or Formula Ib can have a purity of at least about 99.1%, and include less than about 0.04% Impurity A. In some embodiments, the compound of Formula I, Formula Ia, or Formula Ib can have a purity of at least about 99.5%, and include less than about 0.04% Impurity A. In some embodiments, the compound of Formula I, Formula Ia, or Formula Ib can have a purity of at least about 99.5%, and include less than about 0.04% Impurity A.

In some embodiments, the compound of Formula I, Formula Ia, or Formula Ib is a micronized form. In some embodiments, the micronized form has a $d_{90}$ of less than 50 µm. For example, the micronized form has a $d_{90}$ of less than 45 µm, 40 µm, 35 µm, 30 µm, 25 µm, 20 µm, 15 µm, 10 µm, 9 µm, 8 µm, 7 µm, 6 µm, 5 µm, 4 µm, 3 µm, 2 µm, or 1 µm. In some embodiments, the micronized form has a $d_{90}$ of about 0.1 µm-50 µm, for example, about 0.1 µm-45 µm, 0.1 µm-40 µm, 0.1 µm-35 µm, 0.1 µm-30 µm, 0.1 µm-25 µm, 0.1 µm-20 µm, 0.1 µm-15 µm, 0.1 µm-10 µm, 0.1 µm-9 µm, 0.1 µm-8 µm, 0.1 µm-7 µm, 0.1 µm-6 µm, 0.1 µm-5 µm, 0.1 µm-4 µm, 0.1 µm-3 µm, 0.1 µm-2 µm, about 0.5 µm-50 µm, about 0.5 µm-45 µm, 0.5 µm-40 µm, 0.5 µm-35 µm, 0.5 µm-30 µm, 0.5 µm-25 µm, 0.5 µm-20 µm, 0.5 µm-15 µm, 0.5 µm-10 µm, 0.5 µm-9 µm, 0.5 µm-8 µm, 0.5 µm-7 µm, 0.5 µm-6 µm, 0.5 µm-5 µm, 0.5 µm-4 µm, 0.5 µm-3 µm, 0.5 µm-2 µm, about 1 µm-50 µm, about 1 µm-45 µm, 1 µm-40 µm, 1 µm-35 µm, 1 µm-30 µm, 1 µm-25 µm, 1 µm-20 µm, 1 µm-15 µm, 1 µm-10 µm, 1 µm-9 µm, 1 µm-8 µm, 1 µm-7 µm, 1 µm-6 µm, 1 µm-5 µm, 1 µm-4 µm, 1 µm-3 µm, or 1 µm-2 µm. In some embodiments, the micronized form has a $d_{90}$ of ≤about 10 µm, for example ≤about 5 µm. In some embodiments, the micronized form has a $d_{90}$ of about 1 µm-10 µm, for example about 0.1 µm-5 µm. In some embodiments, the micronized form has a $d_{90}$ of about 0.1 µm-5 µm. In some embodiments, the micronized form has a $d_{90}$ of about 4 µm-5 µm.

In some embodiments, the micronized form has a $d_{50}$ of less than 30 µm. For example, the micronized form has a $d_{50}$ of less than 25 µm, 20 µm, 15 µm, 10 µm, 9 µm, 8 µm, 7 µm, 6 µm, 5 µm, 4 µm, 3 µm, 2 µm, or 1 µm. In some embodiments, the micronized form has a $d_{50}$ of about 0.1 µm-30 µm, for example, about 0.1 µm-25 µm, 0.1 µm-20 µm, 0.1 µm-15 µm, 0.1 µm-10 µm, 0.1 µm-9 µm, 0.1 µm-8 µm, 0.1 µm-7 µm, 0.1 µm-6 µm, 0.1 µm-5 µm, 0.1 µm-4 µm, 0.1 µm-3 µm, 0.1 µm-2 µm, 0.1 µm-1 µm, 0.5 µm-30 µm, about 0.5 µm-25 µm, 0.5 µm-20 µm, 0.5 µm-15 µm, 0.5 µm-10 µm, 0.5 µm-9 µm, 0.5 µm-8 µm, 0.5 µm-7 µm, 0.5 µm-6 µm, 0.5 µm-5 µm, 0.5 µm-4 µm, 0.5 µm-3 µm, 0.5 µm-2 µm, 0.5 µm-1 µm, 1 µm-30 µm, 1 µm-25 µm, 1 µm-20 µm, 1 µm-15 µm, 1 µm-10 µm, 1 µm-9 µm, 1 µm-8 µm, 1 µm-7 µm, 1 µm-6 µm, 1 µm-5 µm, 1 µm-4 µm, 1 µm-3 µm, or 1 µm-2 µm. In some embodiments, the micronized form has a $d_{50}$ of about 1 µm-10 µm. In some embodiments, the micronized form has a $d_{50}$ of about 1 µm-5 µm. In some embodiments, the micronized form has a $d_{50}$ of about 4 µm, 3 µm, 2 µm, or 1 µm. In some embodiments, the micronized form has a $d_{50}$ of about 3 µm-4 µm.

In some embodiments, the micronized form has a $d_{10}$ of less than 20 µm. For example, the micronized form has a $d_{10}$ of less than 15 µm, 10 µm, 9 µm, 8 µm, 7 µm, 6 µm, 5 µm, 4 µm, 3 µm, 2 µm, 1 µm, 0.5 µm, 0.4 µm, 0.3 µm, 0.2 µm, or 0.1 µm. In some embodiments, the micronized form has a $d_{10}$ of about 0.1 µm-20 µm, for example, about 1 µm-20 µm, 1 µm-15 µm, 1 µm-10 µm, 1 µm-9 µm, 1 µm-8 µm, 1 µm-7 µm, 1 µm-6 µm, 1 µm-5 µm, 1 µm-4 µm, 1 µm-3 µm, 1 µm-2 µm, 0.1 µm-15 µm, 0.1 µm-10 µm, 0.1 µm-9 µm, 0.1 µm-8 µm, 0.1 µm-7 µm, 0.1 µm-6 µm, 0.1 µm-5 µm, 0.1 µm-4 µm, 0.1 µm-3 µm, 0.1 µm-2 µm, or 0.1 µm-1 µm. In some embodiments, the micronized form has a $d_{10}$ of about 0.1 µm-10 µm. In some embodiments, the micronized form has a $d_{10}$ of about 0.1 µm-5 µm. In some embodiments, the micronized form has a $d_{10}$ of about 0.5 µm-5 µm. In some embodiments, the micronized form has a $d_{10}$ of about 4 µm, 3 µm, 2 µm, 1 µm, 0.9 µm, 0.8 µm, 0.7 µm, 0.6 µm, 0.5 µm, 0.4 µm, 0.3 µm, 0.2 µm, or 0.1 µm. In some embodiments, the micronized form has a $d_{10}$ of about 1 µm-3 µm.

In some embodiments, the compound of Formula I, Formula Ia, or Formula Ib is not micronized (also referred to as non-micronized or unmicronized).

2. Phospholipids

Any suitable amount of phospholipids may be used in the instant pharmaceutical formulations. In some embodiments, the weight ratio of the amount of phospholipids and the compound of Formula I in the pharmaceutical formulation is about 1:1-50:1. In some embodiments, the weight ratio of the amount of phospholipids and the compound of Formula I in the formulation is about 1:1-30:1. In some embodiments, the weight ratio of the amount of phospholipids and the compound of Formula I in the formulation is about 1:1-20:1. In some embodiments, the weight ratio of the amount of phospholipids and the compound of Formula I in the formulation is about 10:1-50:1. In some embodiments, the weight ratio of the amount of phospholipids and the compound of Formula I in the formulation is about 10:1-30:1. In some embodiments, the weight ratio of the amount of phospholipids and the compound of Formula I in the formulation is about 10:1-20:1. In some embodiments, the weight ratio of the amount of phospholipids and the compound of Formula I in the formulation is about 15:1.

a. Phosphatidyl Choline

The pharmaceutical formulations provided herein comprise phospholipids, where in the phospholipids comprise a phosphatidyl choline. In certain embodiments, the phosphatidylcholine is selected from the group consisting of Egg PC (EPC), Soy PC (SPC), 1,2-Dierucoyl-sn-Glycero-3-Phosphatidylcholine (DEPC), dioleoyl phosphatidyl choline (DOPC), distearoyl phosphatidyl choline (DSPC), dimyristoyl phosphatidylcholine (DMPC), dipalmitoyl phosphatidylcholine (DPPC), palmitoyl oleoyl phosphatidylcholine (POPC), hydrogenated soya phosphatidylcholine (HSPC) and combinations thereof. In certain embodiments, the phosphatidylcholine is selected from the group consisting of Egg PC (EPC), Soy PC (SPC), 1,2-Dierucoyl-sn-Glycero-3-Phosphatidylcholine (DEPC), dioleoyl phosphatidyl choline (DOPC), distearoyl phosphatidyl choline (DSPC), dimyristoyl phosphatidylcholine (DMPC), dipalmitoyl phosphatidylcholine (DPPC), palmitoyl oleoyl phosphatidylcholine (POPC) and hydrogenated soya phosphatidylcholine (HSPC).

In certain embodiments, the phosphatidylcholine is selected from the group consisting of EPC, SPC, DEPC, DOPC, DSPC, DMPC, HSPC and combinations thereof. In certain embodiments, the phosphatidylcholine is selected from the group consisting of EPC, SPC, DEPC, DOPC, DSPC, DMPC, and HSPC. In certain embodiments, the phosphatidylcholine is selected from the group consisting of EPC, SPC, DEPC, DOPC, and combinations thereof. In certain embodiments, the phosphatidylcholine is selected from the group consisting of EPC, SPC, DEPC, and DOPC. In certain embodiments, the phosphatidylcholine is selected from the group consisting of EPC, SPC, and combinations thereof. In certain embodiments, the phosphatidylcholine is selected from the group consisting of EPC and SPC. In some embodiments, the phosphatidylcholine is EPC. In some embodiments, the phosphatidylcholine is SPC.

The Soy PC used in the instant pharmaceutical formulations comprise a variety of mono-, di-, tri-unsaturated, and saturated fatty acids. In some embodiments, the Soy-PC comprise palmitic acid in an amount of about 12% to about 33% by weight; stearic acid present in an amount of about 3% to about 8% by weight; oleic acid present in an amount of about 4% to about 22% by weight; linoleic acid present in an amount of about 55% to about 80% by weight; and linolenic acid present in an amount of about 5% to about 10% by weight. In some embodiments, the Soy-PC comprise palmitic acid in an amount of about 12% to about 17% by weight; stearic acid present in an amount of about 2% to about 5% by weight; oleic acid present in an amount of about 7% to about 12% by weight; linoleic acid present in an amount of about 59% to about 70% by weight; and linolenic acid present in an amount of about 5% to about 8% by weight.

The Egg PC used in the instant pharmaceutical formulations comprises palmitic acid in an amount of about 34% by weight; stearic acid in an amount of about 10% by weight; oleic acid in an amount of about 31% by weight; and linoleic acid in an amount of about 18% by weight.

In some embodiment at least about 40% of the fatty-acid chains of the phosphatidyl choline used in the instant pharmaceutical formulations comprise 16 or more carbon atoms. In some embodiments at least about 50% of the fatty-acid chains of the phosphatidyl choline comprise 16 or more carbon atoms. In some embodiments at least about 60% of the fatty-acid chains of the phosphatidyl choline comprise 16 or more carbon atoms. In some embodiment at least about 70% of the fatty-acid chains of the phosphatidyl choline comprise 16 or more carbon atoms. In some embodiments at least about 80% of the fatty-acid chains of the phosphatidyl choline comprise 16 or more carbon atoms. In some embodiments at least about 90% of the fatty-acid chains of the phosphatidyl choline comprise 16 or more carbon atoms. In some embodiments at least about 95% of the fatty-acid chains of the phosphatidyl choline comprise 16 or more carbon atoms. In some embodiments at least about 98% of the fatty-acid chains of the phosphatidyl choline comprise 16 or more carbon atoms. In some embodiments at least about 99% of the fatty-acid chains of the phosphatidyl choline comprise 16 or more carbon atoms. In some embodiments, about 12-17% of the fatty-acid chains of the phosphatidyl choline comprise 16 or more carbon atoms.

In some embodiment at least about 40% of the fatty-acid chains of the phosphatidyl choline comprise 18 or more carbon atoms. In some embodiments at least about 50% of the fatty-acid chains of the phosphatidyl choline comprise 18 or more carbon atoms. In some embodiments at least about 60% of the fatty-acid chains of the phosphatidyl choline comprise 18 or more carbon atoms. In some embodiment at least about 70% of the fatty-acid chains of the phosphatidyl choline comprise 18 or more carbon atoms. In some embodiments at least about 80% of the fatty-acid chains of the phosphatidyl choline comprise 18 or more carbon atoms. In some embodiments at least about 90% of the fatty-acid chains of the phosphatidyl choline comprise 18 or more carbon atoms. In some embodiments at least about 95% of the fatty-acid chains of the phosphatidyl choline comprise 18 or more carbon atoms. In some embodiments at least about 98% of the fatty-acid chains of the phosphatidyl choline comprise 18 or more carbon atoms. In some embodiments at least about 99% of the fatty-acid chains of the phosphatidyl choline comprise 18 or more carbon atoms. In some embodiments, at least about 72-95% of the fatty acid chains of the phosphatidyl choline comprise 18 or more carbon atoms.

In another embodiment at least 50% of the fatty-acid chains of the phosphatidyl choline comprise at least one double bond per chain. In some embodiments at least 60% of the fatty-acid chains of the phosphatidyl choline comprise at least one double bond per chain. In some embodiments at least 70% of the fatty-acid chains of the phosphatidyl choline comprise at least one double bond per chain. In some embodiments at least 75% of the fatty-acid chains of the phosphatidyl choline comprise at least one double bond per chain. In some embodiments at least 80% of the fatty-acid chains of the phosphatidyl choline comprise at least one double bond per chain. In some embodiments at least 85% of the fatty-acid chains of the phosphatidyl choline comprise at least one double bond per chain. In some embodiments at least 90% of the fatty-acid chains of the phosphatidyl choline comprise at least one double bond per chain. In some embodiments at least 95% of the fatty-acid chains of the phosphatidyl choline comprise at least one double bond per chain. In some embodiments at least 7-12% of the fatty-acid chains of the phosphatidyl choline comprise at least one double bond per chain.

In some embodiments at least 50% of the fatty-acid chains of the phosphatidyl choline comprise at least two double bonds per chain. In some embodiments at least 60% of the fatty-acid chains of the phosphatidyl choline comprise at least two double bonds per chain. In some embodiments at least 70% of the fatty-acid chains of the phosphatidyl choline comprise at least two double bonds per chain. In some embodiments at least 75% of the fatty-acid chains of the phosphatidyl choline comprise at least two double bonds per chain. In some embodiments at least 80% of the fatty-acid chains of the phosphatidyl choline comprise at least two double bonds per chain. In some embodiments at least 85% of the fatty-acid chains of the phosphatidyl choline comprise at least two double bonds per chain. In some embodiments at least 90% of the fatty-acid chains of the phosphatidyl choline comprise at least two double bonds per chain. In some embodiments at least 95% of the fatty-acid chains of the phosphatidyl choline comprise at least two double bonds per chain. In some embodiments at least 64-78% of the fatty-acid chains of the phosphatidyl choline comprise at least two double bonds per chain.

b. Anionic Phospholipid

The phospholipids in the pharmaceutical formulations disclosed herein further comprise an anionic phospholipid. Non limiting example of the anionic phospholipids that may be used in the instant pharmaceutical formulations disclosed herein include phosphatidylinositol (PI), phosphatidic acid (PA), phosphatidylglycerol (PG), and phosphatidylserine (PS). In some examples, the anionic phospholipid is a phosphatidic acid, phosphatidylglycerol, or phosphatidylserine.

In some embodiments, the anionic phospholipids used in the instantly disclosed formulations comprise mainly $C_{16}$ or larger fatty-acid chains. In some embodiments, the anionic phospholipids used in the instantly disclosed formulations comprise mainly $C_{17}$ or larger fatty-acid chains. In some embodiments, the anionic phospholipids used in the instantly disclosed formulations comprise mainly Cis or larger fatty-acid chains.

In some embodiments at least about 60% of the fatty-acid chains of the anionic phospholipid comprise 16 or more carbon atoms. In another embodiment at least about 70% of the fatty-acid chains of the anionic phospholipid comprise 16 or more carbon atoms. In another embodiment at least about 80% of the fatty-acid chains of the anionic phospholipid comprise 16 or more carbon atoms. In some embodiments at least about 90% of the fatty-acid chains of the anionic phospholipid comprise 16 or more carbon atoms. In some embodiments at least about 95% of the fatty-acid chains of the anionic phospholipid comprise 16 or more carbon atoms. In some embodiments at least about 99% of the fatty-acid chains of the anionic phospholipid comprise 16 or more carbon atoms.

In some embodiments at least about 60% of the fatty-acid chains of the anionic phospholipid comprise 17 or more carbon atoms. In some embodiments at least about 70% of the fatty-acid chains of the anionic phospholipid comprise 17 or more carbon atoms. In some embodiments at least about 80% of the fatty-acid chains of the anionic phospholipid comprise 17 or more carbon atoms. In some embodiments at least about 90% of the fatty-acid chains of the anionic phospholipid comprise 17 or more carbon atoms. In some embodiments at least about 95% of the fatty-acid chains of the anionic phospholipid comprise 17 or more carbon atoms. In some embodiments at least about 99% of the fatty-acid chains of the anionic phospholipid comprise 17 or more carbon atoms.

In some embodiments at least about 60% of the fatty-acid chains of the anionic phospholipid comprise 18 or more carbon atoms. In some embodiments at least about 70% of the fatty-acid chains of the anionic phospholipid comprise 18 or more carbon atoms. In some embodiments at least about 80% of the fatty-acid chains of the anionic phospholipid comprise 18 or more carbon atoms. In some embodiments at least about 90% of the fatty-acid chains of the anionic phospholipid comprise 18 or more carbon atoms. In some embodiments at least about 95% of the fatty-acid chains of the anionic phospholipid comprise 18 or more carbon atoms. In some embodiments at least about 99% of the fatty-acid chains of the anionic phospholipid comprise 18 or more carbon atoms.

In some embodiments at least about 60% of the fatty-acid chains of the anionic phospholipid comprise 16-18 carbon atoms. In some embodiments at least about 70% of the fatty-acid chains of the anionic phospholipid comprise 16-18 carbon atoms. In some embodiments at least about 80% of the fatty-acid chains of the anionic phospholipid comprise 16-18 carbon atoms. In some embodiments at least about 90% of the fatty-acid chains of the anionic phospholipid comprise 16-18 carbon atoms. In some embodiments at least about 95% of the fatty-acid chains of the anionic phospholipid comprise 16-18 carbon atoms. In some embodiments at least about 99% of the fatty-acid chains of the anionic phospholipid comprise 16-18 carbon atoms.

In some embodiments the anionic phospholipid is selected from Egg-Phosphatidyglycerol (Egg-PG), Soy-Phosphatidylglycerol (Soy-PG), Distearoyl Phosphatidyglycerol (DSPG), Dipalmitoyl Phosphatidyglycerol (DPPG), Dielaidoyl Phosphatidyglycerol (DEPG), Dioleoyl Phosphatidyglycerol (DOPG), Distearoyl Phosphatidic Acid (DSPA), Dipalmitoyl Phosphatidic Acid (DPPA), Dielaidoy Phosphatidic Acid (DEPA), Dioleoyl Phosphatidic Acid (DOPA), Distearoyl Phosphatidylserine (DSPS), Dipalmitoyl Phosphatidylserine (DPPS), Dielaidoy Phosphatidylserine (DEPS), and Dioleoyl Phosphatidylserine (DOPS), and mixtures thereof.

In some embodiments, the anionic phospholipid comprises a phosphatidylglycerol. In some embodiments the anionic phospholipid is selected from the group consisting of Egg-PG, Soy-PG, DSPG, DPPG, DOPG, and mixtures thereof. In some embodiments, the anionic phospholipid comprises Egg-PG. In some embodiments, the anionic phospholipid comprises Soy-PG. In some embodiments, the anionic phospholipid comprises DSPG. In some embodiments, the anionic phospholipid comprises DPPG. In some embodiments, the anionic phospholipid comprises DOPG.

In some embodiments, the anionic phospholipid comprises a phosphatidic acid (PA). In some embodiments the anionic phospholipid is selected from a group consisting of DSPA, DPPA, DEPA, and mixtures thereof. In some embodiments, the anionic phospholipid comprises DSPA. In some embodiments, the anionic phospholipid comprises DPPA. In some embodiments, the anionic phospholipid comprises DEPA.

In some embodiments, the anionic phospholipid comprises a phosphatidylserine (PS). In some embodiments the anionic phospholipid is selected from a group consisting of DSPS, DPPS, DEPS, DOPS and mixtures thereof. In some embodiments, the anionic phospholipid comprises DSPS. In some embodiments, the anionic phospholipid comprises DPPS. In some embodiments, the anionic phospholipid comprises DEPS. In some embodiments, the anionic phospholipid comprises DOPS. In some embodiments the anionic phospholipid comprises DOPS.

Any suitable amounts of phosphatidyl choline and anionic phospholipid can be present in the instant formulations. In some embodiments the phosphatidyl choline and anionic phospholipid are present in a weight ratio of about 1:10 to about 50:1. In some embodiments, the phosphatidyl choline and anionic phospholipid are present in a weight ratio of about 1:1 to about 40:1. In some embodiments, the phosphatidyl choline and anionic phospholipid are present in a weight ratio of about 1:1 to about 30:1. In some embodiments, the phosphatidyl choline and anionic phospholipid are present in a weight ratio of about 1:1 to about 20:1. In some embodiments, the phosphatidyl choline and anionic phospholipid are present in a weight ratio of about 5:1 to about 15:1. In some embodiments, the phosphatidyl choline and anionic phospholipid are present in a weight ratio of about 10:1.

3. Sucrose

The formulations described herein further comprise sucrose. Any suitable amount of sucrose can be used. In some examples, the amount of sucrose is sucrose about 1% to about 25%. In some examples, the amount of sucrose is sucrose about 7% to about 20%. In some examples, the amount of sucrose is sucrose about 7-8%. In some examples, the amount of sucrose is sucrose about 9%. In some examples, the amount of sucrose is sucrose about 17-19%. In some examples, the amount of sucrose is sucrose about 18%.

4. Buffer

In some embodiments, the pharmaceutical formulations described herein may also comprise a pH adjusting agent (or a buffering agent). Without wishing to be bound by theory, in some embodiments, the buffering agent are used to adjust or maintain the pH of pharmaceutical composition to a desired range. In some embodiments, the buffering agent (1) to provide an environment for a better product stability, (2) to provide better comfort for the patient at administration (extreme pH may create irritation and/or discomfort to the site of administration), and/or (3) provide a pH range for better anti-microbial preservative activity.

The pharmaceutical formulations of the disclosure may be formulated with one or more pharmaceutically acceptable buffering agents so that, the pH of the pharmaceutical composition is between about 3 to about 8, for example between 3 to about 7, between 3 to about 6.5, between 3 to about 6.0, between 3 to about 5.5, between 3 to about 5, between 3.5 to about 4.5, or between 4 to about 5. Examples of the buffering agents that may be used include, but are not limited to, hydrochloric acid, sulfuric acid, nitric acid, acetic acid, phosphoric acid, fumaric acid, citric acid, tartaric acid, maleic acid, succinic acid, ammonia solution, ammonium carbonate, sodium borate, sodium carbonate, triethanolamine, trolamine and sodium hydroxide.

In some embodiments, the buffering agent is an acetate buffer. In some embodiments, the pharmaceutical composition has a pH of about 3 to about 6 and the buffering agent is an acetate buffer. In some embodiments, the pharmaceutical composition has a pH of about 3 to about 5 and the buffering agent is an acetate buffer. In some embodiments, the pharmaceutical composition has a pH of about 3.5 to about 4.5 and the buffering agent is an acetate buffer. In some embodiments, the pharmaceutical composition has a pH of about 4 and the buffering agent is an acetate buffer. In some embodiments, the acetate buffer comprises acetic acid and sodium acetate or a combination thereof.

5. Lyophilized Pharmaceutical Formulations

The composition of the present invention also includes a lyophilized or dehydrated composition of the compound of Formula I, or a pharmaceutically acceptable salt thereof, and phospholipids wherein the phospholipids comprise a phosphatidyl choline and an anionic phospholipid. In some embodiments, the present invention provides a lyophilized composition comprising the compound of Formula Ia, or a pharmaceutically acceptable salt thereof, and phospholipids wherein the phospholipids comprise a phosphatidyl choline and an anionic phospholipid. The lyophilized composition can be in any suitable solid form, such as a powder. In some embodiments, the lyophilized composition comprises about 1-10% w/v of the compound of Formula I, about 20-50% w/v of PC, about 1-5% w/v of PG, and 50-70% w/v of sucrose. In some embodiments, the lyophilized composition comprises about 2% w/v of the compound of Formula I, about 32% w/v of PC, about 3% w/v of PG, and 63% w/v of sucrose.

The lyophilized composition can be contained in any suitable container, such as a sealed vial. In some embodiments, the present invention provides a sealed vial containing the lyophilized composition.

The lyophilized pharmaceutical formulations can be prepared by any appropriate manner. For example, the formulations can be dehydrated by heating the sample to a suitable temperature for a suitable period of time. The formulations can also be dehydrated under a reduced pressure atmosphere at any suitable temperature. The reduced pressure atmosphere can be any pressure less than atmospheric pressure. The reduced pressure atmosphere can be heated to a temperature above room temperature, be maintained at about room temperature, or cooled to a temperature below room temperature. For example, the formulations can be cooled to a temperature of less than room temperature while under a reduced pressure atmosphere. Suitable temperatures include, but are not limited to, less than room temperature, or less than 20° C., 15° C., 10° C., 5° C., 0° C., −5° C., −10° C., −15° C., −20° C., −25° C., −30° C., −40° C., −50° C., −55° C., −60° C., −65° C., −70° C., −75° C., or −80° C. When a reduced pressure atmosphere is used, the reduced pressure atmosphere can be less than atmospheric pressure, or less than 100 torr (mm Hg), 50, 25, 10, 5, 4.58 (the triple point for water), 4, 3, 2, 1, 0.5, 0.1, 0.05, or less than 0.01 torr. The formulations can be cooled to a temperature of less than 0.01° C. while under a reduced pressure atmosphere of less than 4.58 torr (611 Pascal or 0.006 atmospheres).

IV. Methods of Preparing the Pharmaceutical Formulations

The compositions of the present invention can be prepared according to the methods described in the examples below and variations thereof understood by one of skill in the art. For example, the instant pharmaceutical formulations of the present invention can be prepared by (a) dissolving the compound of Formula I and the phospholipids in a suitable solvent. In some embodiments, the method of making the instant pharmaceutical formulations further comprise (b) removing the solvent to obtain an intermediate formulation. In some embodiments, the solvents are removed under reduced pressure. In some embodiments, the method of making the instant pharmaceutical formulations further comprise (c) hydrating the intermediate formulation with and an aqueous solution of sucrose and (d) optionally adjusting the pH using a buffering agent. In some embodiments, the methods of making the instant pharmaceutical formulations further comprise (e) homogenizing and/or filtering the pharmaceutical formulation. In some embodiments, the methods of making the instant pharmaceutical formulations further comprise (f) lyophilizing the pharmaceutical formulation to obtain a lyophilized pharmaceutical formulation.

Any suitable solvent can be used in preparation of the instant pharmaceutical formulations. In some embodiments, the solvent is a mixture of an alcohol solvent (e.g., methanol, ethanol, and propanol) and an haloalkane (e.g., dichloromethane or chloroform). In some embodiments, the solvent is a mixture of methanol and chloroform.

V. Methods of Use

The present disclosure also provides a method of treating or preventing a viral infection in a subject (e.g., human) in need thereof, the method comprising administering to the subject a pharmaceutical formulation described herein.

In some embodiments, the present disclosure provides a method of treating a viral infection in a subject (e.g., human) in need thereof, the method comprising administering to a subject in need thereof a pharmaceutical formulation described herein.

In some embodiments, the present disclosure provides for methods of treating or preventing a viral infection in a subject (e.g., human) in need thereof, the method comprising administering to the subject a pharmaceutical formulation disclosed herein and at least one additional active therapeutic agent.

In some embodiments, the present disclosure provides for methods of treating a viral infection in a subject (e.g., human) in need thereof, the method comprising administering to the subject a pharmaceutical formulation disclosed herein and at least one additional active therapeutic agent.

In some embodiments, the present disclosure provides for methods of inhibiting a viral polymerase in a cell, the methods comprising contacting the cell infected a virus with a pharmaceutical formulation disclosed herein, whereby the viral polymerase is inhibited.

In some embodiments, the present disclosure provides for methods of inhibiting a viral polymerase in a cell, the methods comprising contacting the cell infected a virus with a pharmaceutical formulation disclosed herein, and at least one additional active therapeutic agent, whereby the viral polymerase is inhibited.

Also provided here are the uses of the pharmaceutical formulations disclosed herein for use in treating or preventing a viral infection in a subject in need thereof. For example, provided herein are uses of the pharmaceutical formulations disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a human in need thereof, the method comprising administering to the human a pharmaceutical formulation disclosed herein. Paramyxoviridae viruses include, but are not limited to Nipah virus, Hendra virus, measles, mumps, and parainfluenza virus.

In some embodiments, the viral infection is a pneumoviridae virus infection. As such, in some embodiments, the present disclosure provides a method of treating a pneumoviridae virus infection in a human in need thereof, the method comprising administering to the human a pharmaceutical formulation provided herein. Pneumoviridae viruses include, but are not limited to, respiratory syncytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a pharmaceutical formulation disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a pharmaceutical formulation provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a pharmaceutical formulation disclosed herein.

In some embodiments, the present disclosure provides a method for reducing the viral load associated with RSV infection, wherein the method comprises administering to a human infected with RSV a pharmaceutical formulation disclosed herein.

In some embodiments, the viral infection is a picornaviridae virus infection. As such, in some embodiments, the present disclosure provides a method of treating a picornaviridae virus infection in a human in need thereof, the method comprising administering to the human a pharmaceutical formulation of the present disclosure. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection.

In some embodiments, the present disclosure provides a pharmaceutical formulation, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a pharmaceutical composition described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection.

In some embodiments, the flaviviridae virus infection is a West Nile virus infection. In some embodiments, the flaviviridae virus infection is a zika virus infection. In some embodiments, the flaviviridae virus infection is a Japanese encephalitis virus infection. In some embodiments, the flaviviridae virus infection is a hepatitis C virus infection.

In some embodiments, the present disclosure provides use of a pharmaceutical formulation disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human pharmaceutical formulation disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a pharmaceutical formulation for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a pharmaceutical formulation provided herein. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. The pharmaceutical formulations provided herein are useful for treatment of all SARS-CoV-2 infections (COVID-19), for example for the treatment of mild, moderate, or severe SARS-CoV-2 infection. In some embodiments, the pharmaceutical formulations provided herein are used for treatment of severe SARS-CoV-2 infection. In some embodiments, the pharmaceutical formulations provided herein are used for treatment of moderate SARS-CoV-2 infection. In some embodiments, the pharmaceutical formulations provided herein are used for treatment of mild SARS-CoV-2 infection. In some embodiments, the pharmaceutical formulations provided herein are used for treatment of early stage SARS-CoV-2 infection when the virus is primarily replicated in the upper respiratory tract of the subject.

In some embodiments, the present disclosure provides a pharmaceutical formulation for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection.

In some embodiments, the viral infection is an arenaviridae virus infection. As such, in some embodiments, the disclosure provides a method of treating an arenaviridae virus infection in a human in need thereof, the method comprising administering to the human a pharmaceutical formulation disclosed herein. In some embodiments, the arenaviridae virus infection is a Lassa infection or a Junin infection.

In some embodiments, the present disclosure provides a pharmaceutical formulation for use in the treatment of a arenaviridae virus infection in a human in need thereof. In some embodiments, the arenaviridae virus infection is a Lassa infection or a Junin infection.

In some embodiments, the viral infection is an orthomyxovirus infection, for example an influenza virus infection. In some embodiments, the viral infection is an influenza virus A, influenza virus B, or influenza virus C infection.

The pharmaceutical formulations provided herein are also useful for treatment and or prevention of viral infections in humans with compromised renal function. In some examples, the pharmaceutical formulations provided herein are used for treatment and or prevention of a viral infection in humans with an estimated glomerular filtration rate (eGFR) eFGR of less than 90, for examples an eFGR of 60-89, 45-59, 30-44, 15-29, or less than 15. In some examples, the pharmaceutical formulations provided herein are used for treatment and or prevention of a viral infection in humans with an eFGR of less than 30, for example an eFGR of 15-29. In some examples, the pharmaceutical formulations provided herein are used for treatment and or prevention of a viral infection in humans with an eFGR of less than 15.

As described more fully herein, the pharmaceutical formulation described herein can be administered with one or more additional therapeutic agent(s) to an individual (e.g., a human) infected with a viral infection. The additional therapeutic agent(s) can be administered to the infected individual at the same time as the pharmaceutical formulation of the present disclosure or before or after administration of the pharmaceutical formulation of the present disclosure.

VI. Routes of Administration

The pharmaceutical formulations of the present disclosure, can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient.

A pharmaceutical formulation of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the pharmaceutical formulation is administered on a daily or intermittent schedule for the duration of the individual's life. In some embodiments, the pharmaceutical formulation is administered for about one day to about 2 weeks. In some embodiments, the pharmaceutical formulation is administered for about one day to about 10 days. In some embodiments, the pharmaceutical formulation is administered for about one day to about 5 days. In some embodiments, the pharmaceutical formulation is administered for about one day to about 3 days. In some embodiments, the pharmaceutical formulation is administered for about one day. In some embodiments, the pharmaceutical formulation is administered for about two days.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of the compound of Formula I (e.g., the compound of Formula Ia or the compound of Formula Ib) per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of the compound of Formula I (e.g., the compound of Formula Ia or the compound of Formula Ib) described herein administered per dose or per day. Daily dosage of the compound of Formula I (e.g., the compound of Formula Ia or the compound of Formula Ib), or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 50 to 400 mg/day, between about 50 to 500 mg/day, between 50-600 mg/day, between 50-700 mg/day, between 50-800 mg/day. In some embodiments, the daily dosage of the compound of Formula I (e.g., the compound of Formula Ia or the compound of Formula Ib) is about 50-150 mg/day. In some embodiments, the daily dosage of the compound of Formula I (e.g., the compound of Formula Ia or the compound of Formula Ib) is about 150-250 mg/day. In some embodiments, the daily dosage of the compound of Formula I (e.g., the compound of Formula Ia or the compound of Formula Ib) is about 500-700 mg/day.

The dosage or dosing frequency of a pharmaceutical formulation of the present disclosure may be adjusted over the course of the treatment, based on the judgment of the administering physician.

The pharmaceutical formulations of the present disclosure may be administered to an individual (e.g., a human) in a therapeutically effective amount. In some embodiments, the pharmaceutical formulation is administered once daily.

The pharmaceutical formulations provided herein can be administered by any useful route and means, such as by oral or parenteral (e.g., intramuscular, subcutaneous, or intravenous) administration. In some embodiments, the pharmaceutical formulations provided herein are administered orally. In some embodiments, the pharmaceutical formulations provided herein are administered by parenteral administration. In some embodiments, the pharmaceutical formulations provided herein are administered by intramuscular, subcutaneous, or intravenous administration. In some embodiments, the pharmaceutical formulations provided herein are administered by intramuscular administration. In some embodiments, the pharmaceutical formulations provided herein are administered by subcutaneous. In some embodiments, the pharmaceutical formulations provided herein are administered by intravenous administration.

VII. Combination Therapy

The compounds described herein can also be used in combination with one or more additional therapeutic agents. As such, also provided herein are methods of treatment of the a viral infection in a subject in need thereof, wherein the methods comprise administering to the subject a pharmaceutical formulation disclosed therein and a therapeutically effective amount of one or more additional therapeutic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine, or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpirnase, nafamostat, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682 (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some examples, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fos- amprenavir, darunavir, tipranavir, cobicistat. In some examples, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lamivudine, bictegravir and combinations thereof. In some embodiment, the additional therapeutic agent is bictegravir. In some examples, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some examples, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras (G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vagta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccines (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a 2019-nCov vaccine.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is a PD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASC09F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5]decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of 2019-nCoV virus antibody.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immunomodulatory medications (e.g., interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine.

In some examples, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimumab, inflixinab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g., azithromycin, clarithromycin, and *Mycoplasma pneumoniae*), fluoroquinolones (e.g., ciprofloxacin and levofloxacin), tetracyclines (e.g., doxycycline and tetracycline), or a combination thereof.

In some embodiments, the compounds disclosed herein are used in combination with pneumonia standard of care (see e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells.

In some examples, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some examples, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some examples, the additional therapeutic agent is carrimycin, suramin, triazavirin, dipyridamole, bevacizumab, meplazumab, GD31 (rhizobium), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially. In general, during alternation therapy, an effective dosage of each active ingredient is administered sequentially, i.e., serially, whereas in combination therapy, effective dosages of two or more active ingredients are administered together. A synergistic antiviral effect denotes an antiviral effect which is greater than the predicted purely additive effects of the individual compounds of the combination.

1. Combination Therapy for the Treatment of Pneumoviridae

The pharmaceutical formulations provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The pharmaceutical formulations provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the pharmaceutical formulations provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumethasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2, 3-Dihydro-benzofuran-5-yl)-ethyl]-pyrrolidin-3-yl}-2,2-di-phenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The pharmaceutical formulations provided herein may also be combined with mucolytic agents to treat both the infection and symptoms of respiratory infections. A non-limiting example of a mucolytic agent is ambroxol. Similarly, the pharmaceutical formulations may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the virus infection is complicated with bronchiolitis. The combination of the pharmaceutical formulation provided herein with hypertonic saline may also comprise any of the additional agents discussed above. In one embodiment, nebulized about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The pharmaceutical formulations provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, an Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The pharmaceutical formulations provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The pharmaceutical formulations provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

VIII. EXAMPLES

Example 1. Exemplary Lipid-Based Formulation of Remdesivir with 18% Sucrose, 5 mM Acetate Buffer Soy-PC, DSPG and Remdesivir were dissolved in a 1:1 (v:v) mixture of methanol and chloroform at a molar ratio of Soy-PC:DSPG of 1:0.1 and a weight ratio of (Soy-PC+DSPG):remdesivir of 15:1. Once all components were dissolved, solvents were removed by evaporation under continuous vacuum in a vacuum tray dryer for not less than 5 days. The intermediate paste were then hydrated in 18% sucrose and 5 mM acetate pH 4 buffer at 40-60° C. at desired drug concentrations. The hydrated solution was homogenized at 40-60° C. at 5-10 kpsi to form liposomes. The resulting solution was filtered through a 0.2-micron filter, filled into vials and lyophilized. The final lyophilized cake is diluted with water at a target concentration (PC: 68 mg/mL; Formula Ia: 5 mg/mL; PG: 7 mg/mL) of the final formulation.

Example 2. Exemplary Lipid-Based Formulation of Remdesivir with 9% Sucrose, 10 mM Acetate Buffer Soy-PC, DSPG and remdesivir were dissolved in a 1:1 (v:v) mixture of methanol and chloroform at a molar ratio of Soy-PC:DSPG of 1:0.1 and a weight ratio of (Soy-PC+DSPG):remdesivir of 15:1. Once all components were dissolved, solvents were removed by evaporation under continuous vacuum in a vacuum tray dryer for not less than 5 days. The intermediate paste was then hydrated in 9% sucrose and 10 mM acetate pH 4 buffer at 40-60° C. at desired drug concentrations. The hydrated solution was homogenized at 40-60° C. at 5-10 kpsi to form liposomes. The resulting solution was filtered through a 0.2-micron filter, filled into vials and lyophilized. The final lyophilized cake is diluted with water at a target concentration (PC: 34 mg/mL; Formula Ia: 2.5 mg/mL; PG: 3.5 mg/mL) of the final formulation.

Example 3. Pharmacokinetic Summary

The ability of a lipid-based dispersion of the invention to successfully deliver the compound of Formula Ia (remdesivir, GS-5734) was evaluated using a pharmacokinetic study described below. The 9% sucrose formulation form above was used.

Cynomolgus monkeys were dosed intravenously with a liposomal formulation of remdesivir. For comparison, monkeys were also dosed with a cyclodextrin formulation ("the reference formulation") of remdesivir described in WO2019/014247. Animals (n=3) were dosed at 10 mg/kg for remdesivir. Blood samples were drawn after dosing. Samples were then analyzed for the compound of Formula Ia, Compound A (GS-441524), and Compound B (GS-704277), and levels in plasma.

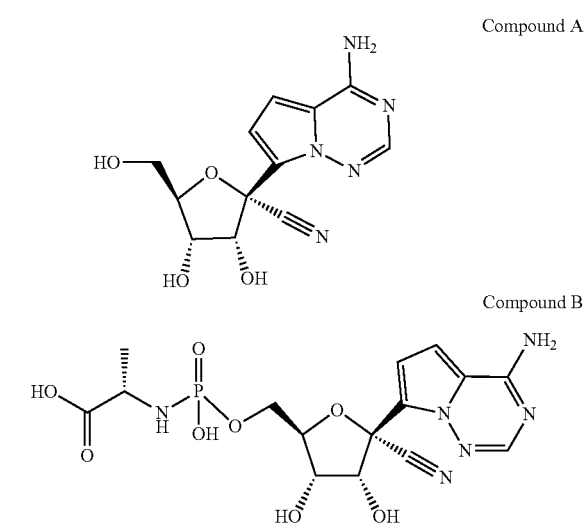

Figure 2:
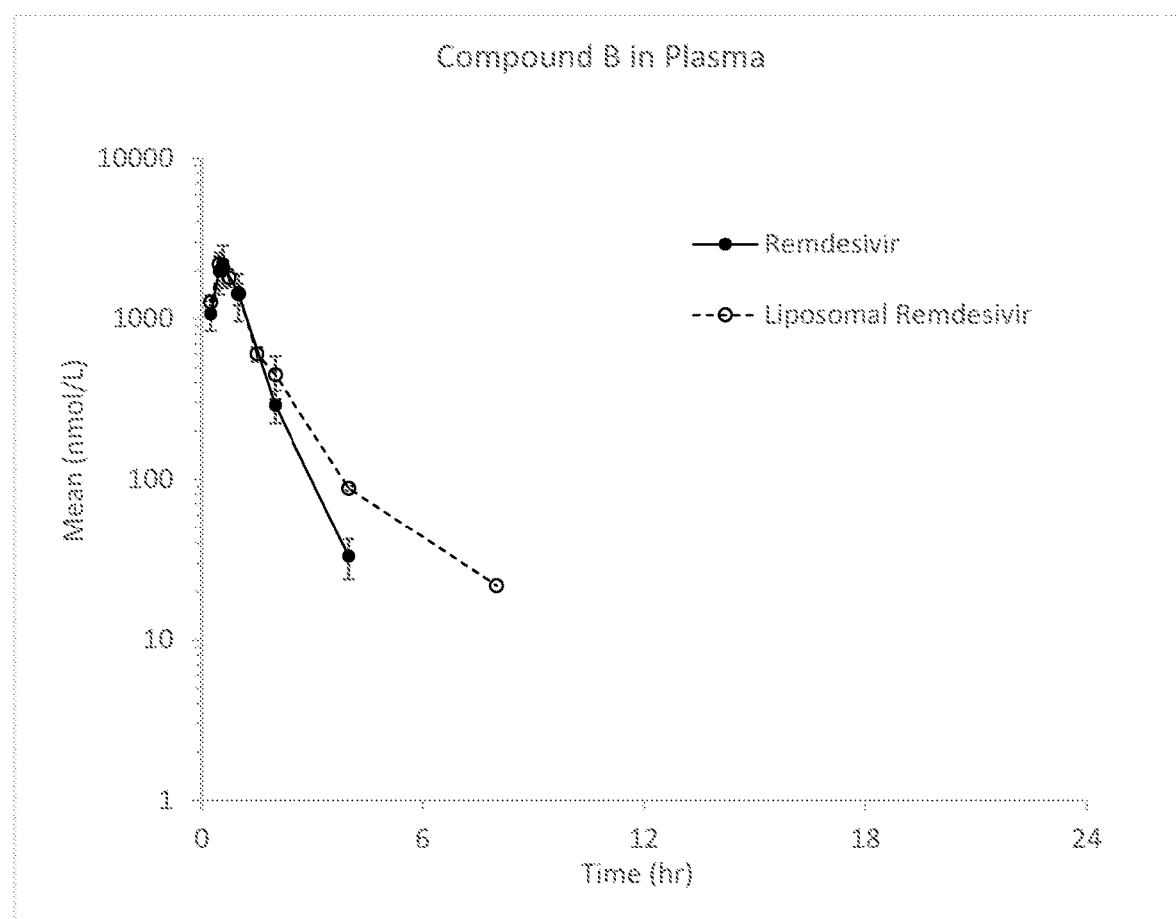
FIG. 2. Shows concentration-time profiles of Compound B (a metabolite of the compound of Formula Ia) in plasma following administration of an exemplary pharmaceutical formulation (10 mg/kg dosing of the compound of Formula Ia) to Cynomolgus monkeys.
Figure 3:
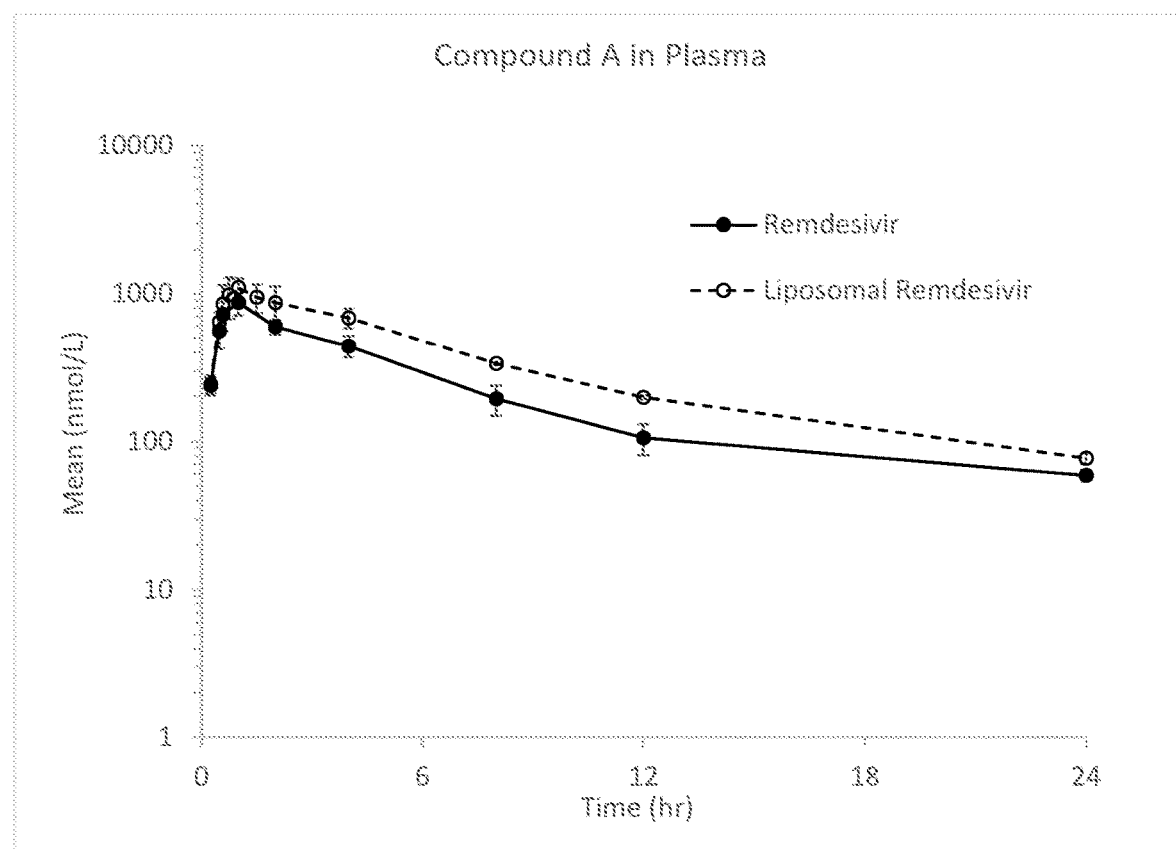
FIG. 3. Shows concentration-time profiles of Compound A (a metabolite of the compound of Formula Ia) in plasma following administration of an exemplary pharmaceutical formulation (10 mg/kg dosing of the compound of Formula Ia) to Cynomolgus monkeys.

Representative data from the PK study is shown in FIGS. 1-3. This data demonstrates that the phospholipid comprising formulations of the instant application appear equivalent to the reference formulation in $C_{max}$ and in AUC as well as clearance of the drug.

Example 4. Exemplary Liquid Formulation of the Compound of Formula Ia with 9% Sucrose and 5 mM Acetate Buffer Liquid composition was prepared using 15:1, lipids to Formula Ia weight ratio (lipids include Distearoylphosphatidylglycerol (DSPG) and Soy Phosphatidylcholine (Soy-PC)) and 1:0.1, Soy-PC to DSPG molar ratio in 9% sucrose and 5 mM sodium acetate. Final liquid drug concentration was 5 mg/ml pH range from 3.5 to 5.5.

Example 5. Stability Studies

Aqueous liposome suspensions are often difficult to store over long periods time due to potential liposome aggregation and fusion, as well as hydrolysis of lipid components. Lyophilization allows the formulation to achieve maximum shelf-life stability. The presence of sucrose as an excipient in the liposomal remdesivir formulation serves to stabilize the integrity of the physical structure of the liposome during lyophilization. Thus, the formulations can be lyophilized under appropriate conditions, and the lyophilized cake can be reconstituted with sterile water.

Studies were performed in order to evaluate the effect of lyophilization in the stability of the liposome formulation. The stability of two formulations, one liquid and one lyophilized, were monitored under an accelerated stability condition (40° C., t=4 weeks) by analyzing the known and unknown degradant levels and the remdesivir concentrations (target %). The known impurities studied included phenol, Compounds A and B in Example 3, as well as the following compounds:

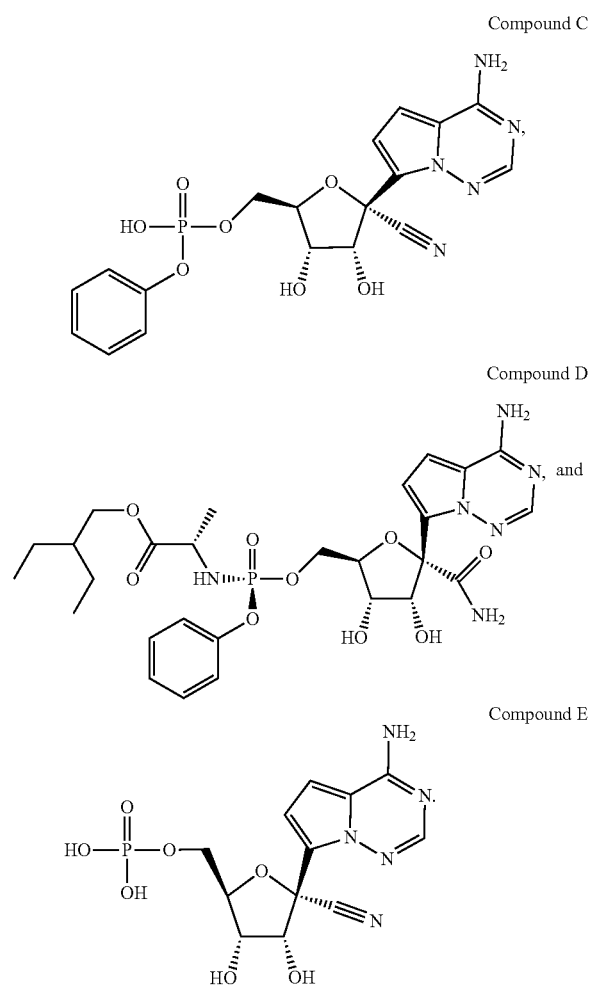

Figure 4:
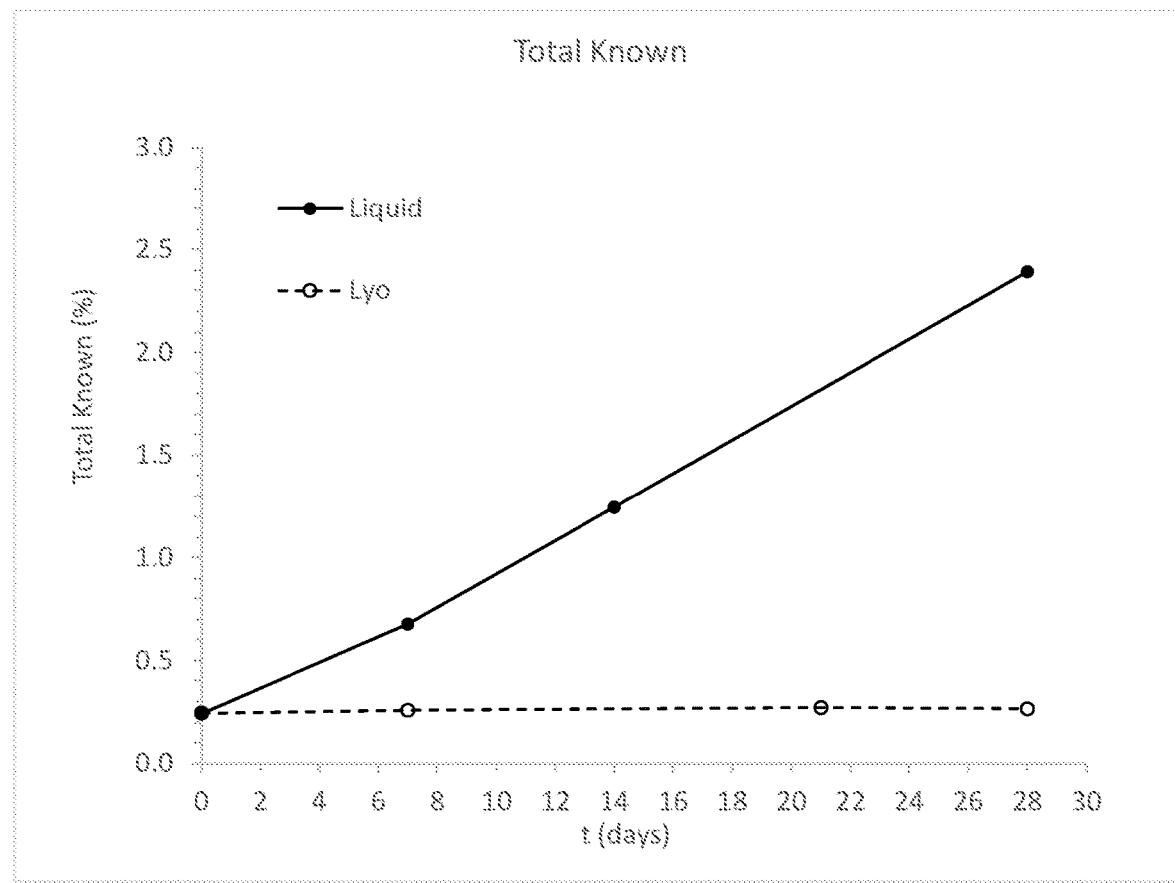
FIG. 4. Shows comparison of total known impurities observed in exemplary lyophilized and solution formulations upon storage at 40° C. for 4 weeks.
Figure 5:
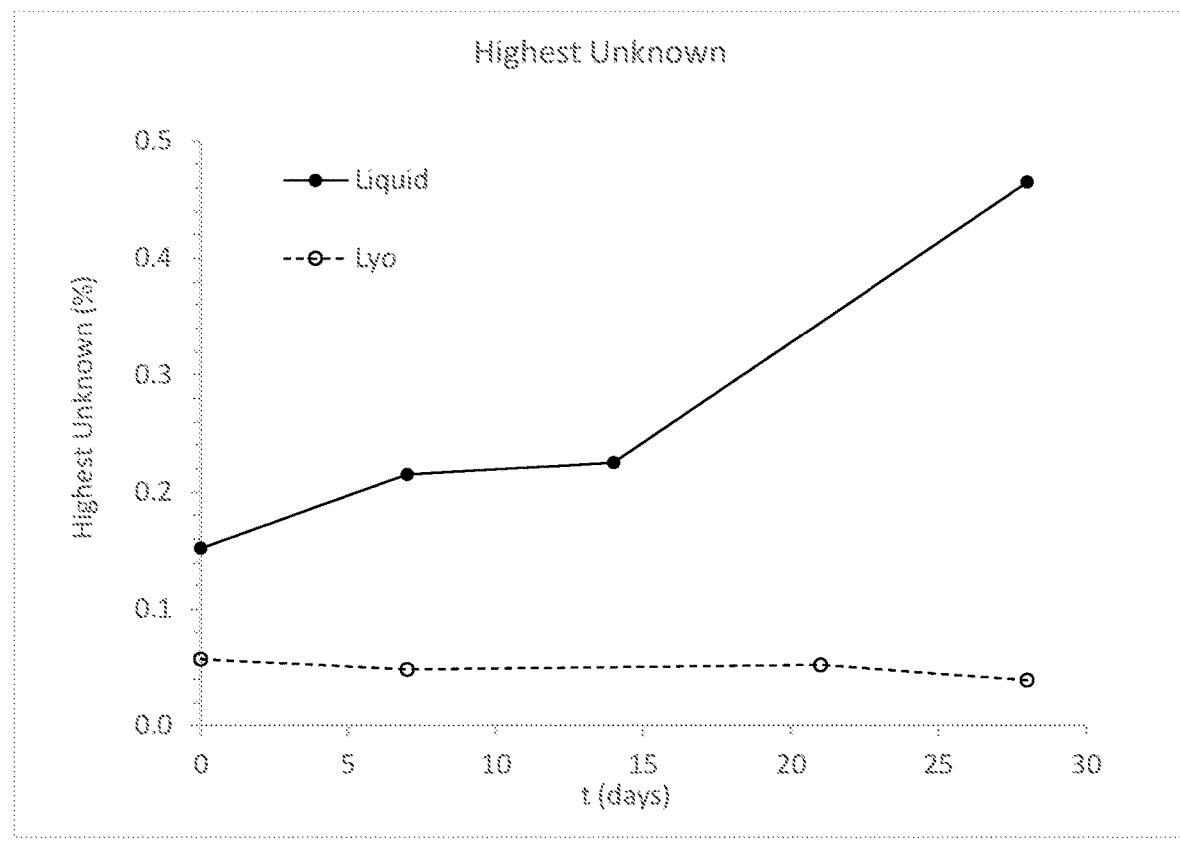
FIG. 5. Shows comparison of an unknown (highest unknown) impurity observed in exemplary lyophilized and solution formulations upon storage at 40° C. for 4 weeks.
Figure 6:
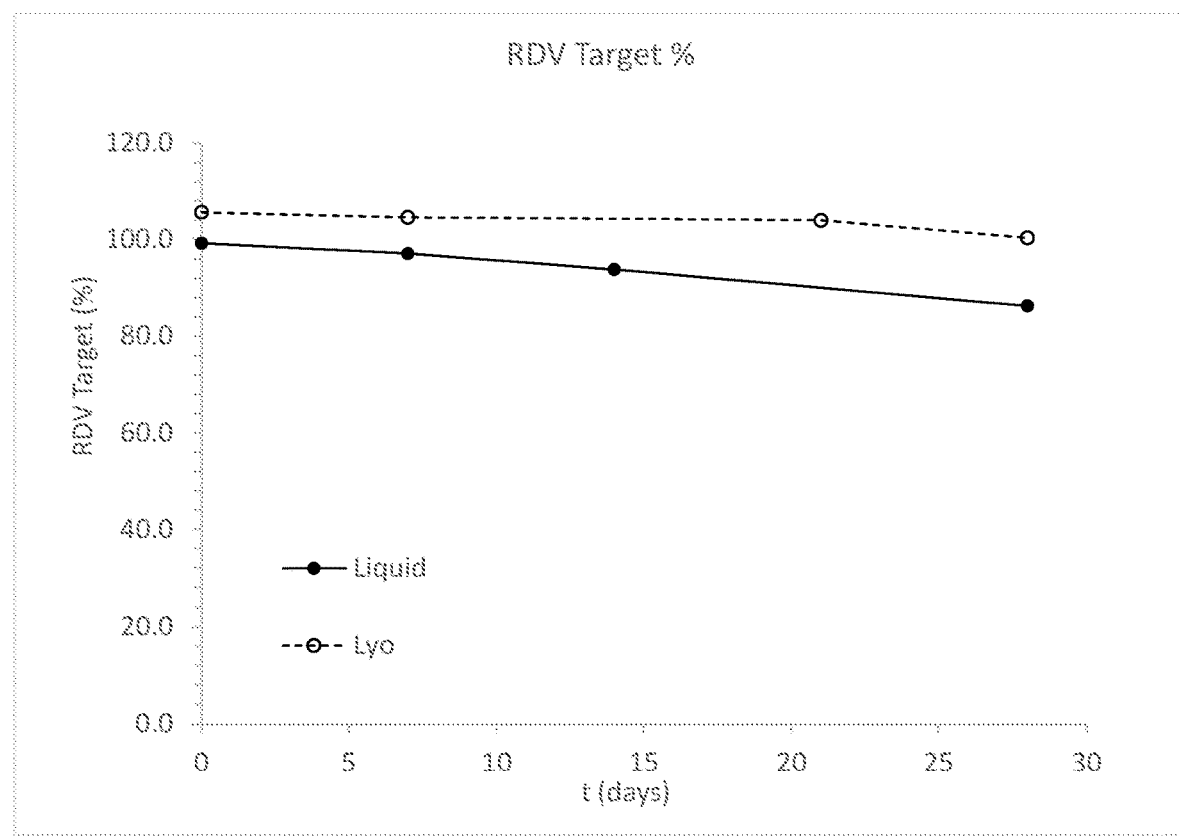
FIG. 6. Shows comparison of the amount of the compound of Formula Ia observed in exemplary lyophilized and solution formulations upon storage at 40° C. for 4 weeks (calculated against label claim mg/mL over mg/mL).

Representative data from the stability studies are shown in FIGS. 4-6. This demonstrates that the lyophilized preparation clearly protects the product against degradation into known and unknown substances, when compared to that of an equivalent liquid form.

Example 6. Study of Bulking Agents

Studies were performed in order to evaluate the effect of the bulking agent (sugar) type and concentration in the stability of the liposome formulation. First, the stability of two formulations, one with 9% trehalose and one with 9% sucrose, were monitored under stability (25° C., t=30 days) by analyzing their colloidal properties (absorbance at 600 nm and particle size distribution). Representative data from the stability studies is shown in Table 1 below. This demonstrates that the formulation with 9% trehalose as the bulking agent clearly had inferior colloidal properties, noted by high visible absorbance at 600 nm (A600) values and bimodal particle size distribution, when compared to the 9% sucrose formulation at t=0.

TABLE 1

Colloidal stability results from 9% trehalose and 9% sucrose formulations

| Formulation | Temp | t (days) | A600 | PS (nm) |
|---|---|---|---|---|
| 9% Trehalose | 25° C. | 0 | 0.641 | Bimodal |
| | | 14 | 0.652 | 83.60 |
| | | 30 | 0.668 | Bimodal |
| 9% Sucrose | 25° C. | 0 | 0.382 | 50.20 |
| | | 14 | N/A | N/A |
| | | 30 | N/A | N/A |

Stability of two formulations, one with 9% sucrose and one with 18% sucrose, were monitored under stability (5, 25, 30° C., t=up to 6 months) by analyzing their colloidal properties (absorbance at 600 nm and particle size distribution). Representative data from the stability studies are shown in Table 2. This demonstrates that under the accelerated conditions of 25° C. and 30° C., the samples suffered colloidally and were unable to be fully reconstituted by day 14 and day 7, respectively. In contrast, the 18% sucrose formulation samples under all temperature conditions showed consistently low absorbance values and no bimodal size distributions over time, indicating improved colloidal stability.

TABLE 2

Colloidal stability results from 9% sucrose and 18% sucrose formulations

| Formulation | Temp | t (days) | A600 | PS (nm) |
|---|---|---|---|---|
| 9% Sucrose | 5° C. | 0 | 0.382 | 50.20 |
| | | 30 | 0.368 | 51.10 |
| | | 90 | 0.367 | 51.30 |
| | 25° C. | 0 | 0.382 | 50.20 |
| | | 14 | | N/A |
| | | 30 | | N/A |
| | | 90 | | N/A |
| | 30° C. | 0 | 0.382 | 50.20 |
| | | 7 | | N/A |
| | | 30 | | N/A |
| 18% Sucrose | 5° C. | 0 | 0.173 | 78.00 |
| | | 7 | 0.155 | 60.10 |
| | | 30 | 0.160 | 61.30 |
| | | 90 | 0.157 | 66.00 |
| | | 180 | 0.135 | 56.40 |
| | 25° C. | 0 | 0.173 | 78.00 |
| | | 7 | 0.160 | 66.70 |
| | | 30 | 0.104 | 62.40 |
| | | 90 | 0.156 | 74.00 |
| | | 180 | 0.094 | 58.30 |
| | 30° C. | 0 | 0.173 | 78.00 |
| | | 7 | 0.143 | 68.90 |
| | | 30 | 0.150 | 61.70 |

Example 7. Long Term Stability Study with Large Scale Production of Lipid-Based Formulation of Remdesivir with 18% Sucrose, 5 mM Acetate Buffer Studies are performed to evaluate the stability of the exemplary formulation in Example 1. The stability of the formulation is monitored under a long term stability condition (5° C., t=60 months), an intermediate condition (15-25C, t=60 months), and accelerated condition (25±2C, t=60 months) by analyzing the known and unknown degradant levels, the remdesivir and excipients concentrations, colloidal properties (absorbance at 600 nm and particle size distribution), pH, and water content.

Representative data, for up to 12 months, from the stability studies is shown in Tables 3-5. The stability data for all parameters remains essentially unchanged throughout the 12 month period and samples under all stability conditions remain within the provisional limits throughout the time points tested under all stability conditions.

TABLE 3

Stability result from long term stability condition (5° C.)

| Name | Provisional Limits | t = 0 | t = 3 Months | t = 6 Months | t = 9 Months | t = 12 Months |
|---|---|---|---|---|---|---|
| Average Assay, % | 90-110% | 101 | 102 | 96 | 98 | 103 |
| Mean Alpha tocopherol, mg/vial | NLT 2 mg/vial | 11 | 10 | 10 | 10 | 10 |
| Average Degradant 1 (Compound A), % | NMT 1% | ND | ND | ND | ND | ND |
| Average Degradant 2 (Compound C), % | NMT 1.5% | ND | ND | ND | ND | ND |
| Average Degradant 3 (Compound D), % | NMT 1% | 0.14 | 0.15 | 0.14 | 0.14 | 0.15 |
| Average Total Known Degradant, % | NMT 3% | 0.14 | 0.15 | 0.14 | 0.14 | 0.15 |
| Average Total Unknown Degradant, % | NMT 3% | ND | ND | ND | ND | ND |
| Mean DSPG, mg/vial | — | 149 | 145 | 158 | 174 | 165 |
| Average Median, nm | 10-100 nm | 56 | 60 | 57 | 74 | 72 |
| Average pH | 3.5-6.0 | 5.4 | 5.3 | 5.4 | 5.4 | 5.4 |
| Average Phenol, % | — | ND | ND | ND | ND | ND |
| Average Soy-PC, mg/vial | — | 1397 | 1397 | 1425 | 1407 | 1390 |
| Average UV Spectrum, AU | NMT 1.0 | 0.2 | 0.2 | 0.2 | 0.2 | 0.2 |
| Average Water Content, % | NMT 5% | 1.6 | 1.8 | 2.2 | 1.3 | 1.8 |

NLT = Not less than, NMT = Not more than, ND = Not detected.

TABLE 4

Stability result from intermediate stability condition (15-25° C.)

| Name | Provisional Limits | t = 0 | t = 3 Months | t = 6 Months | t = 9 Months | t = 12 Months |
|---|---|---|---|---|---|---|
| Average Assay, % | 90-110% | 101 | 101 | 97 | 98 | 104 |
| Mean Alpha tocopherol, mg/vial | NLT 2 mg/vial | 11 | 10 | 10 | 10 | 10 |
| Average Degradant 1 (Compound A), % | NMT 1% | ND | ND | ND | ND | ND |
| Average Degradant 2 (Compound C), % | NMT 1.5% | ND | ND | ND | ND | ND |
| Average Degradant 3 (Compound D), % | NMT 1% | 0.14 | 0.15 | 0.14 | 0.15 | 0.18 |
| Average Total Known Degradant, % | NMT 3% | 0.14 | 0.15 | 0.14 | 0.15 | 0.18 |
| Average Total Unknown Degradant, % | NMT 3% | ND | ND | ND | ND | ND |
| Mean DSPG, mg/vial | — | 149 | 145 | 141 | 164 | 158 |
| Average Median, nm | 10-100 nm | 56 | 70 | 66 | 63 | 67 |
| Average pH | 3.5-6.0 | 5.4 | 5.3 | 5.3 | 5.3 | 5.5 |
| Average Phenol, % | — | ND | ND | ND | ND | ND |
| Average Soy-PC, mg/vial | — | 1397 | 1409 | 1414 | 1373 | 1331 |
| Average UV Spectrum, AU | NMT 1.0 | 0.2 | 0.2 | 0.1 | 0.1 | 0.2 |
| Average Water Content, % | NMT 5% | 1.6 | 1.7 | 1.8 | 1.6 | 1.8 |

NLT = Not less than, NMT = Not more than, ND = Not detected.

TABLE 5

Stability result from accelerated stability condition (25 ± 2° C.)

| Name | Provisional Limits | t = 0 | t = 1 Months | t = 3 Months | t = 6 Months | t = 9 Months | t = 12 Months |
|---|---|---|---|---|---|---|---|
| Average Assay, % | 90-110% | 101 | 99 | 100 | 96 | 98 | 101 |
| Mean Alpha tocopherol, mg/vial | NLT 2 mg/vial | 11 | 10 | 10 | 10 | 10 | 10 |

TABLE 5-continued

| | | | Stability result from accelerated stability condition (25 ± 2° C.) | | | | |
|---|---|---|---|---|---|---|---|
| Name | Provisional Limits | t = 0 | t = 1 Months | t = 3 Months | t = 6 Months | t = 9 Months | t = 12 Months |
| Average Degradant 1 (Compound A), % | NMT 1% | ND | ND | ND | ND | ND | ND |
| Average Degradant 2 (Compound C), % | NMT 1.5% | ND | ND | ND | ND | ND | ND |
| Average Degradant 3 (Compound D), % | NMT 1% | 0.14 | 0.15 | 0.15 | 0.15 | 0.16 | 0.15 |
| Average Total Known Degradant, % | NMT 3% | 0.14 | 0.15 | 0.15 | 0.15 | 0.16 | 0.15 |
| Average Total Unknown Degradant, % | NMT 3% | ND | ND | ND | ND | ND | ND |
| Mean DSPG, mg/vial | — | 149 | 153 | 148 | 149 | 188 | 169 |
| Average Median, nm | 10-100 nm | 56 | 65 | 68 | 63 | 63 | 62 |
| Average pH | 3.5-6.0 | 5.4 | 5.3 | 5.3 | 5.3 | 5.3 | 5.5 |
| Average Phenol, % | — | ND | ND | ND | ND | ND | ND |
| Average Soy-PC, mg/vial | — | 1397 | 1398 | 1385 | 1366 | 1298 | 1351 |
| Average UV Spectrum, AU | NMT 1.0 | 0.2 | 0.1 | 0.1 | 0.1 | 0.1 | 0.1 |
| Average Water Content, % | NMT 5% | 1.6 | 1.6 | 1.9 | 1.4 | 2.2 | 1.7 |

NLT = Not less than, NMT = Not more than, ND = Not detected.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments have been described herein for purposes of illustration, various modifications may be made without deviating from the spirit and scope of the disclosure. Accordingly, the disclosure is not limited except as by the appended claims.

What is claimed is:

1. A pharmaceutical formulation comprising:
   a. phospholipids;
   b. a compound of Formula I:

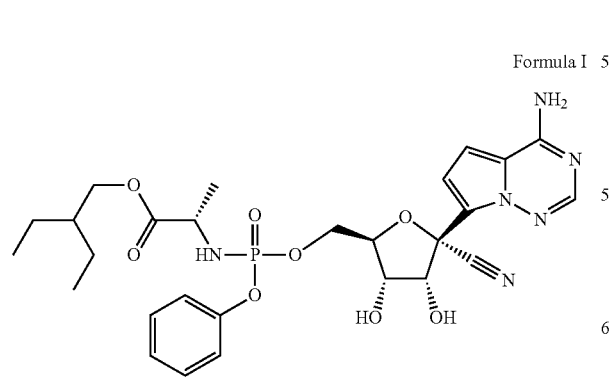

Formula I or a pharmaceutically acceptable salt thereof; and
   c. sucrose;
   wherein the phospholipids comprise a phosphatidyl choline and an anionic phospholipid.

2. The pharmaceutical formulation of claim 1, wherein the compound of Formula I is a compound of Formula Ia:

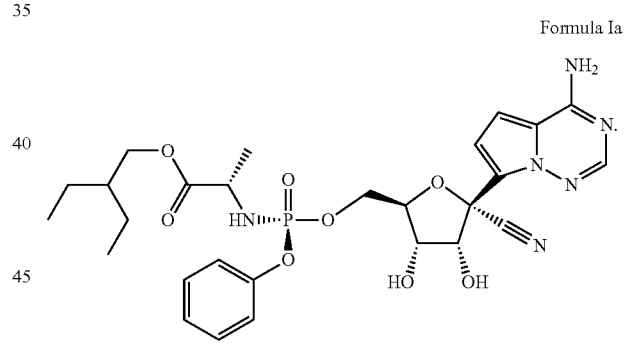

Formula Ia

3. The pharmaceutical formulation of claim 1, wherein at least about 60% of fatty acid chains of the phosphatidyl choline comprise 16 or more carbon atoms.

4. The pharmaceutical formulation of claim 1, wherein at least about 60% of fatty acid chains of the phosphatidyl choline comprise 18 or more carbon atoms.

5. The pharmaceutical formulation of claim 1, wherein at least about 50% of fatty acid chains of the phosphatidyl choline comprise at least one carbon-carbon double bond.

6. The pharmaceutical formulation of claim 1, wherein the phosphatidyl choline is Soy-PC, egg-PC, DEPC, or DOPC.

7. The pharmaceutical formulation of claim 6, wherein the phosphatidyl choline is soy-PC or egg PC.

8. The pharmaceutical formulation of claim 1, wherein at least about 60% of fatty acid chains of the anionic phospholipid choline comprise 14 or more carbon atoms.

9. The pharmaceutical formulation of claim 1, wherein at least about 60% of fatty acid chains of the anionic phospholipid choline comprise 16 or more carbon atoms.

10. The pharmaceutical formulation of claim 1, wherein at least about 60% of fatty acid chains of the anionic phospholipid choline comprise 18 or more carbon atoms.

11. The pharmaceutical formulation of claim 1, wherein the anionic phospholipid is selected form the group consisting of Egg-PG, Soy-PG, DSPG, DEPG, DOPG, DSPA, DPPA, DEPA, DOPA, DSPS, DPPS, DEPS, and DOPS, and mixtures thereof.

12. The pharmaceutical formulation of claim 11, wherein the anionic phospholipid is DSPG.

13. The pharmaceutical formulation of claim 1, wherein the phospholipids and the compound of Formula I are present in a weight ratio of about 5:1 to about 25:1.

14. The pharmaceutical formulation of claim 13, wherein the phospholipids and the compound of Formula I are present in a weight ratio of about 15:1.

15. The pharmaceutical formulation of claim 1, wherein the phosphatidyl choline and the anionic phospholipid are present in a molar ratio of about 1:1 to about 20:1.

16. The pharmaceutical formulation of claim 15, wherein the phosphatidyl choline and the anionic phospholipid are present in a molar ratio of about 10:1.

17. The pharmaceutical formulation of claim 1, further comprising a buffer.

18. The pharmaceutical formulation of claim 1, wherein the sucrose is present in an amount of about 1% to about 25%.

19. The pharmaceutical formulation of claim 18, wherein the sucrose is present in an amount of about 9%.

20. The pharmaceutical formulation of claim 18, wherein the sucrose is present in an amount of about 18%.

21. The pharmaceutical formulation of claim 1, wherein the compound of Formula I is present in an amount of about 0.1 mg/mL to about 20 mg/mL relative to total volume of the pharmaceutical formulation.

22. The pharmaceutical formulation of claim 21, wherein the compound of Formula I is present in an amount of about 6 mg/mL to about 7 mg/mL relative to total volume of the pharmaceutical formulation.

23. The pharmaceutical formulation of claim 22, wherein the compound of Formula I is present in an amount of about 6.67 mg/mL relative to total volume of the pharmaceutical formulation.

24. The pharmaceutical formulation of claim 21, wherein the compound of Formula I is present in an amount of about 1 mg/mL to about 5 mg/mL relative to total volume of the pharmaceutical formulation.

25. The pharmaceutical formulation of claim 24, wherein the compound of Formula I is present in an amount of about 3 mg/mL to about 4 mg/mL relative to total volume of the pharmaceutical formulation.

26. The pharmaceutical formulation of claim 25, wherein the compound of Formula I is present in an amount of about 3.33 mg/mL relative to total volume of the pharmaceutical formulation.

27. The pharmaceutical formulation of claim 1, wherein the pharmaceutical formulation has a pH of about 2.0 to about 7.0.

28. The pharmaceutical formulation of claim 1, wherein the pharmaceutical formulation is a lyophilized formulation.

29. A method of treating or preventing a viral infection in a human in need thereof, the method comprising administering to the human the pharmaceutical formulation of claim 1.

30. The pharmaceutical formulation of claim 13, wherein the phosphatidyl choline and the anionic phospholipid are present in a molar ratio of about 1:1 to about 20:1.

31. The pharmaceutical formulation of claim 14, wherein the phosphatidyl choline and the anionic phospholipid are present in a molar ratio of about 1:1 to about 20:1.

32. The pharmaceutical formulation of claim 13, wherein the phosphatidyl choline and the anionic phospholipid are present in a molar ratio of about 10:1.

33. The pharmaceutical formulation of claim 14, wherein the phosphatidyl choline and the anionic phospholipid are present in a molar ratio of about 10:1.

* * * * *